US009962237B2

(12) United States Patent
Nakashima et al.

(10) Patent No.: US 9,962,237 B2
(45) Date of Patent: May 8, 2018

(54) ROOT CANAL FILLING MATERIAL CONTAINING MESENCHYMAL STEM CELLS AND METHOD FOR REGENERATING DENTAL TISSUE USING THE SAME

(75) Inventors: Misako Nakashima, Obu (JP); Koichiro Iohara, Obu (JP)

(73) Assignee: National Center for Geriatrics and Gerontology, Aichi (JP)

( * ) Notice: Subject to any disclaimer, the term of this patent is extended or adjusted under 35 U.S.C. 154(b) by 1229 days.

(21) Appl. No.: 13/985,111

(22) PCT Filed: Jan. 31, 2012

(86) PCT No.: PCT/JP2012/052155
§ 371 (c)(1),
(2), (4) Date: Jul. 14, 2014

(87) PCT Pub. No.: WO2012/117793
PCT Pub. Date: Sep. 7, 2012

(65) Prior Publication Data
US 2014/0322672 A1 Oct. 30, 2014

(30) Foreign Application Priority Data
Feb. 28, 2011 (JP) ................... 2011-042862

(51) Int. Cl.
*A01N 63/00* (2006.01)
*A61C 5/04* (2006.01)
*A61K 6/00* (2006.01)
*A61L 27/36* (2006.01)
*A61L 27/38* (2006.01)
*A61L 27/54* (2006.01)
*A61C 5/40* (2017.01)
*A61C 5/50* (2017.01)

(52) U.S. Cl.
CPC .................. *A61C 5/04* (2013.01); *A61C 5/40* (2017.02); *A61C 5/50* (2017.02); *A61K 6/0035* (2013.01); *A61K 6/0041* (2013.01); *A61L 27/3633* (2013.01); *A61L 27/3834* (2013.01); *A61L 27/54* (2013.01); *A61L 2300/412* (2013.01); *A61L 2430/12* (2013.01)

(58) Field of Classification Search
None
See application file for complete search history.

(56) References Cited

U.S. PATENT DOCUMENTS

| 2008/0253999 A1 | 10/2008 | Osther et al. |
| 2011/0020310 A1 | 1/2011 | Nakashima et al. |
| 2011/0171607 A1* | 7/2011 | Mao .................. A61C 5/04 433/224 |

FOREIGN PATENT DOCUMENTS

| CN | 101970022 A | 2/2011 |
| EP | 2263706 A1 | 12/2010 |
| JP | 2009-509512 A | 3/2009 |
| JP | 2011-78752 A | 4/2011 |
| WO | WO 2009-078971 A1 | 6/2009 |
| WO | WO 2009-113733 A1 | 9/2009 |

OTHER PUBLICATIONS

Huang et al. Tis Engineer 2010;16:605-15.*
D'Anto et al. JOE 2010;36:1839-43.*
Kuo et al. Artificial Organs 2010;35:113-21.*
Fleischmannova et al. J Dent Res 2010;89:108-115.*
Volponi et al. Trends Cell Biol 2010;20:715-22.*
Wikipedia, Human Tooth Development, updated 2017.*
Mafi et al. Open Orthopaedics J, 2011;5:Suppl 2-M4, pp. 253-260.*
Yang et al. Biomaterials 2007;28:3110-20.*
Chen et al. "A study on differentiation of adipose-derived stem cells into odontoblast-like cells in vitro", *J. Pract Stomatol* 24(1):9-13 (2008).
Dong et al. "In vitro study on the odontogenic differentiation potentiality of bone marrow mesenchymal stem cells", *Chinese J. Conservative Dentistry* 20(4):192-195 (2010).
Office Action corresponding to Chinese Application No. 201280010806.8 dated Jun. 27, 2014.
*Kyushu-Shika-Gakkai-zasshl*, 2008, vol. 62, Issues 3 and 4, pp. 115 to 118.
Office Action corresponding to Japanese Application. No. 2011-042862 dated Sep. 29, 2015.
Lovelace et al. "Evaluation of the Delivery of Mesenchymal Stem Cells into the Root Canal Space of Necrotic Immature Teeth after Clinical Regenerative Endodontic Procedure", *J. Endod* 37(2):133-138 (2011).
Sonoyanna et al. "Mesenchymal Stem Cell-Mediated Functional Tooth Regeneration in Swine", *PLOS ONE* 1.(1):e79 (2006) 8 pages.
Sonoyama et al. "Characterization of the Apical Papilla and its Residing Stem Cells from Human Immature Permanent Teeth: A Pilot Study", j. Endod 34(2):166-171 (2008).
Extended European Search Report corresponding to European Application No. 12752700.0 dated Sep. 27, 2016.

(Continued)

*Primary Examiner* — Janice Li
(74) *Attorney, Agent, or Firm* — Myers Bigel, P.A.

(57) ABSTRACT

A root canal filling material for a tooth extraction or tooth non-extraction process can be used clinically because of its easy availability and can efficiently enhance dental tissue regeneration; a method for regenerating dental tissue using the filling material is also provided. A root canal filling material 200 including mesenchymal stem cells 220 excluding dental pulp stem cells, which are inserted into the apical side of a root canal subjected to pulp extirpation or to root canal enlargement and cleaning of an infected root canal and including an extracellular matrix 210 is provided, and a method for regenerating dental tissue, through a tooth extracting or tooth non-extracting process, including a step of injecting the root canal filling material into the apical side of a root canal of a non-extracted tooth subjected to pulp extirpation or to root canal enlargement and cleaning of an infected root canal is provided.

9 Claims, 22 Drawing Sheets

(56) References Cited

OTHER PUBLICATIONS

Iohara et al. "Dental Pulp Stem Cell Therapy for Dentin Regeneration with Recombinant Human Bone Morphogenetic Protein (BMP) 2", *Nihon Shika Hozongaku Zasshi* 46(5):654-665 (2003).
Laureys et al. "Revascularization after cryopreservation and autotransplantation of immature and mature apicoectomized teeth", *Am J Orthod Dentofacial Orthop* 119:346-352 (2001).
International Search Report corresponding to International Application No. PCT/JP2012/052155 dated Mar. 6, 2012.

\* cited by examiner

FIG.4(a)
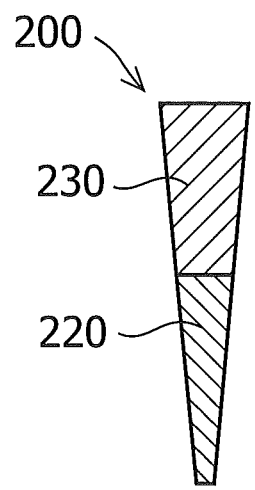
FIG.4(b)
FIG.5
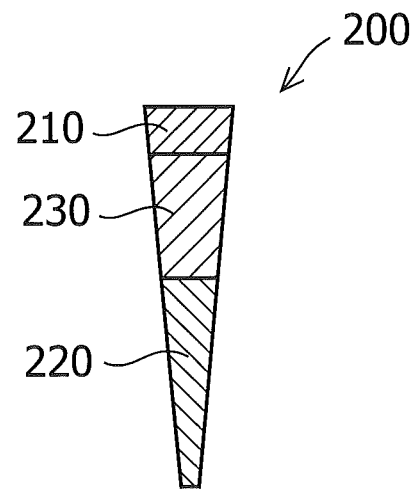
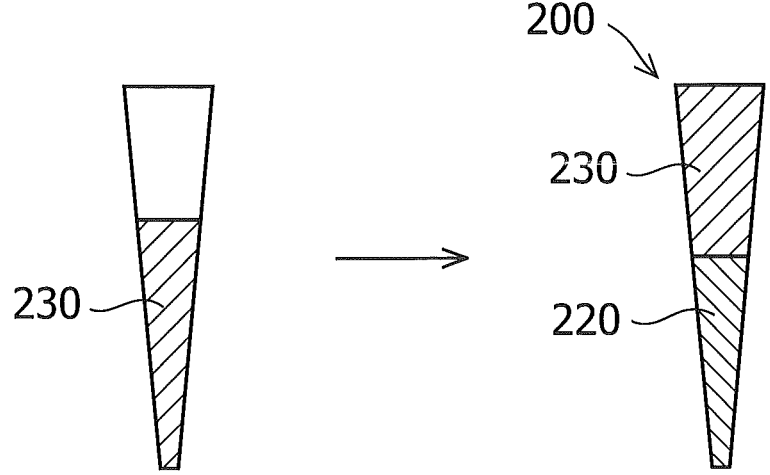

500μm

200μm

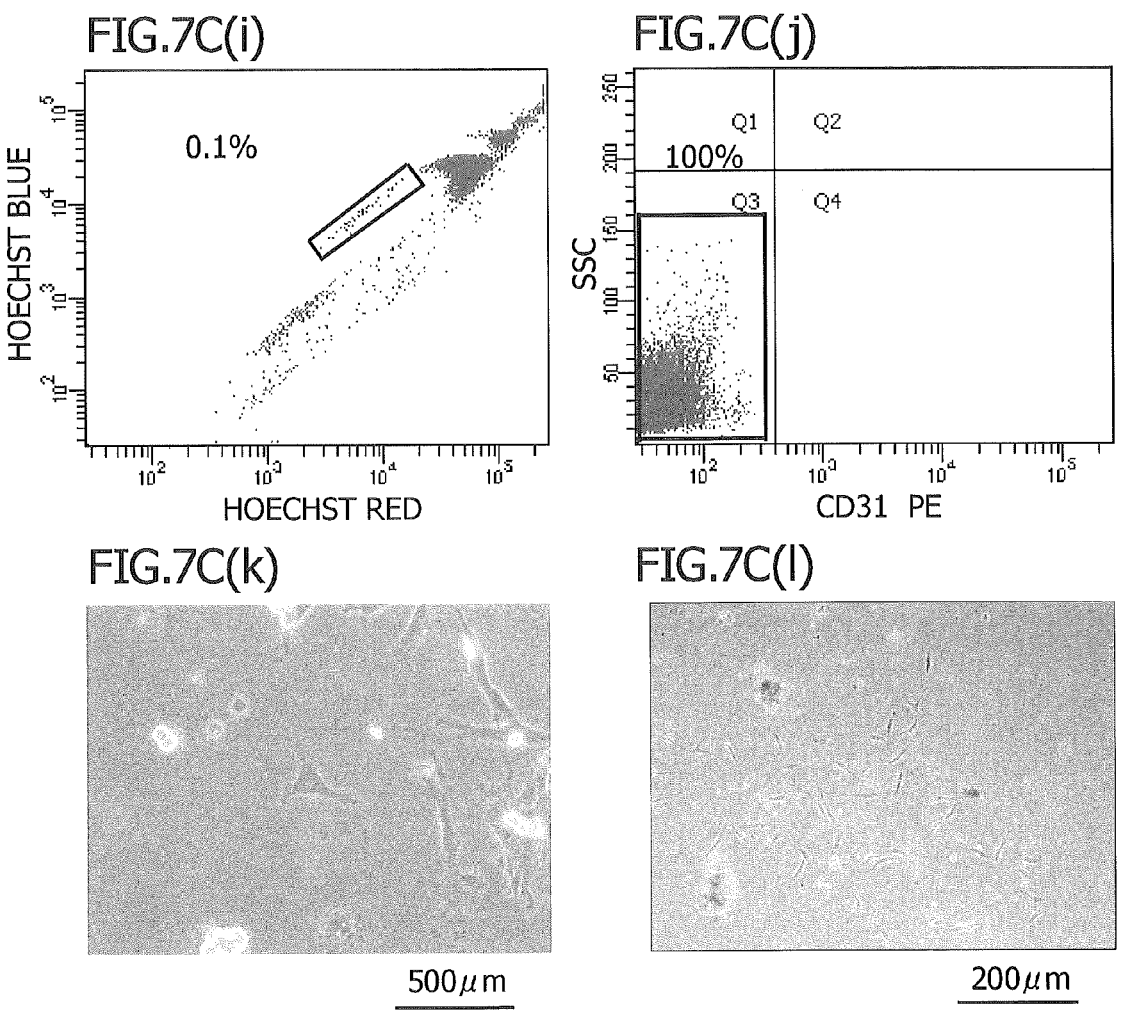

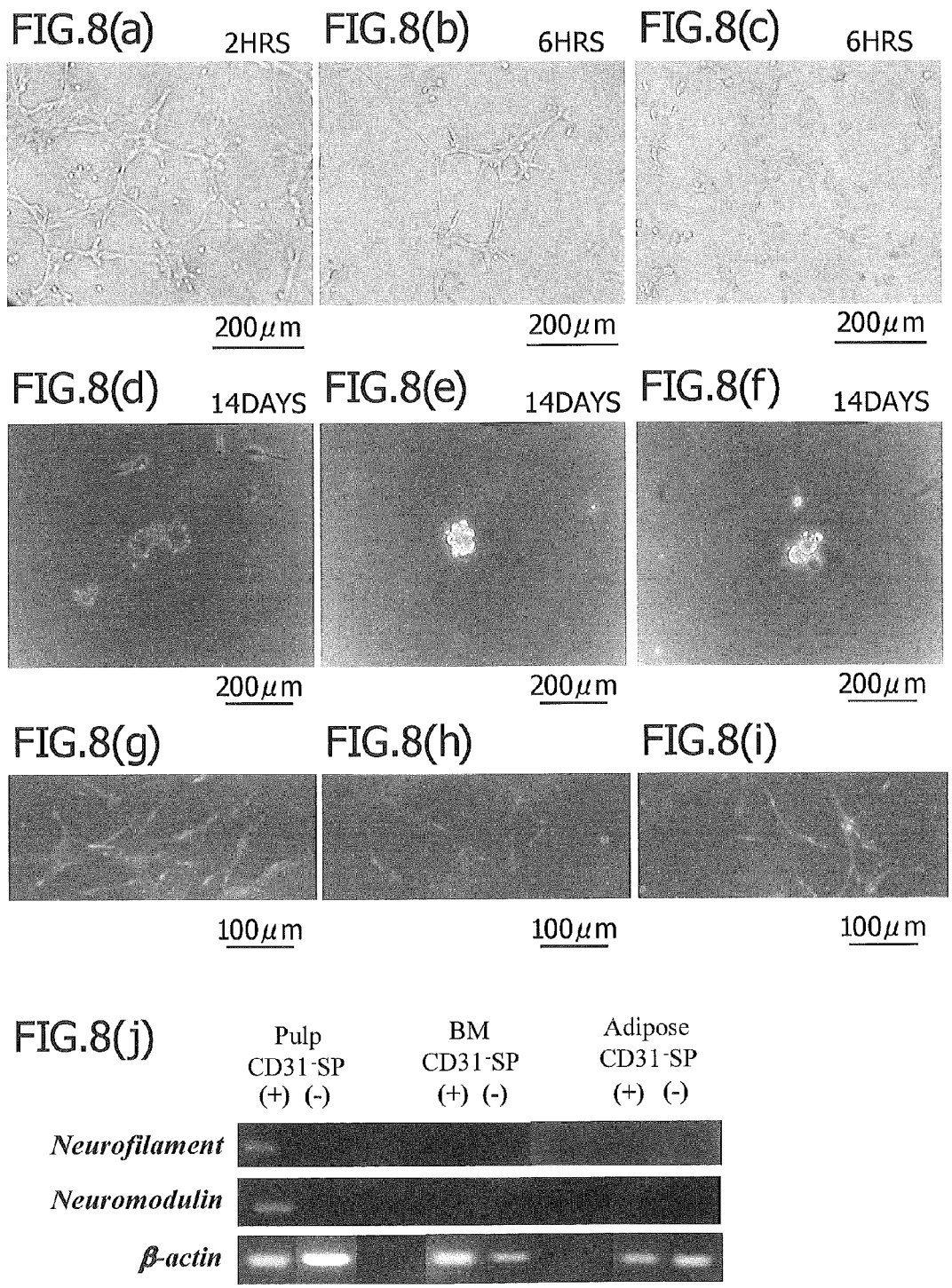

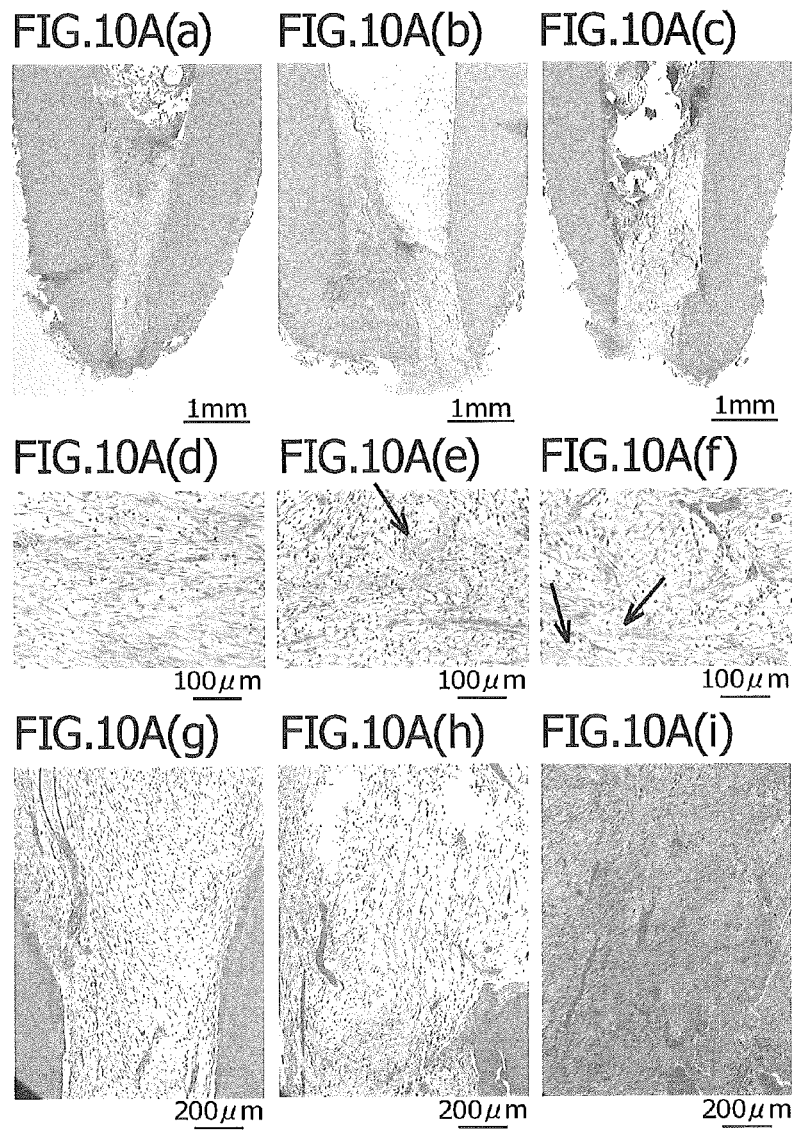
FIG.10A(a) FIG.10A(b) FIG.10A(c)
FIG.10A(d) FIG.10A(e) FIG.10A(f)
FIG.10A(g) FIG.10A(h) FIG.10A(i)
FIG.10A(j)
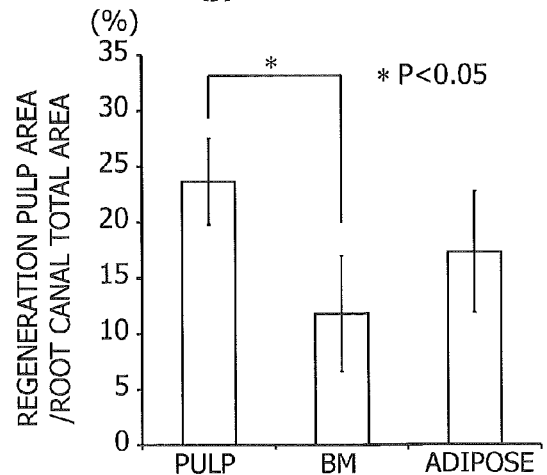
*P<0.05

100μm

100μm

100μm

50μm

50μm

50μm

100μm

100μm

100μm

FIG.11A(a)
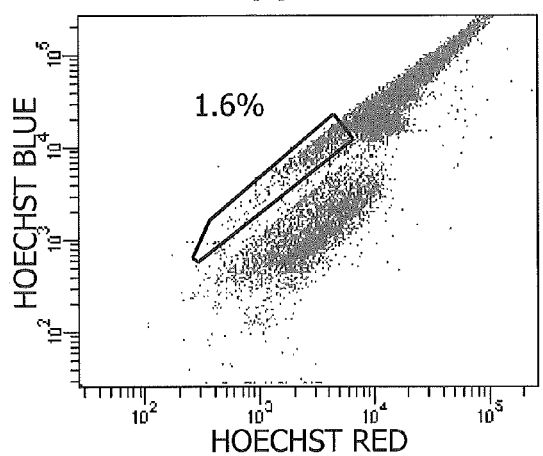
FIG.11A(b)
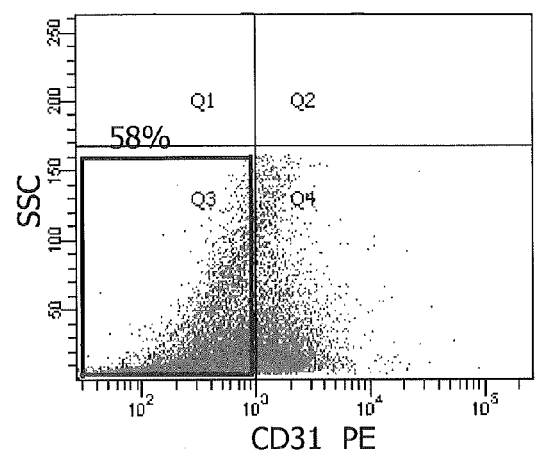
FIG.11A(c)     1 DAY
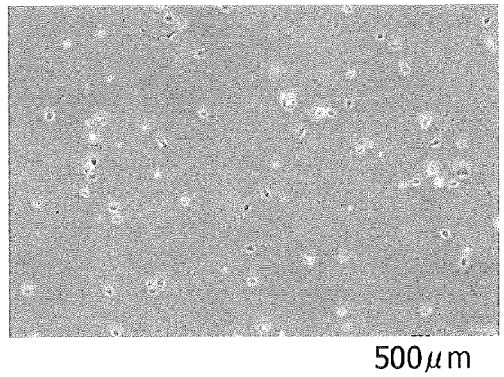
FIG.11A(d)     7 DAYS
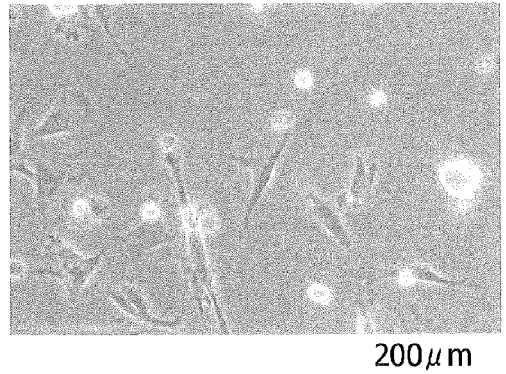

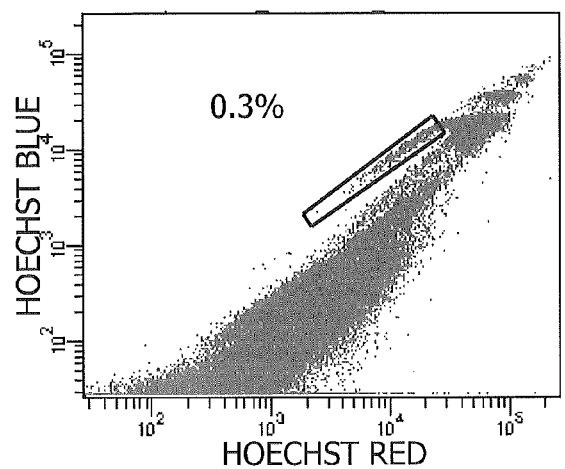
FIG.11B(e)
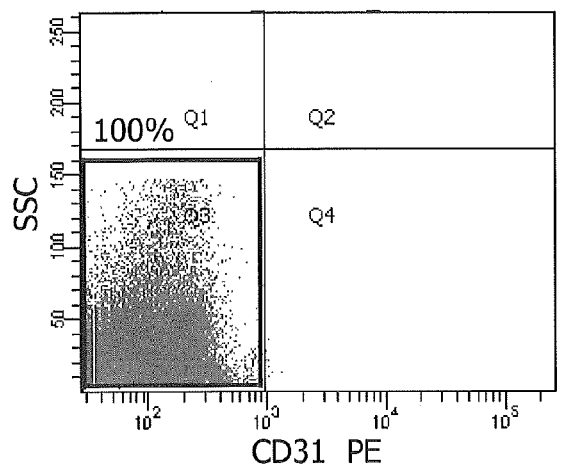
FIG.11B(f)
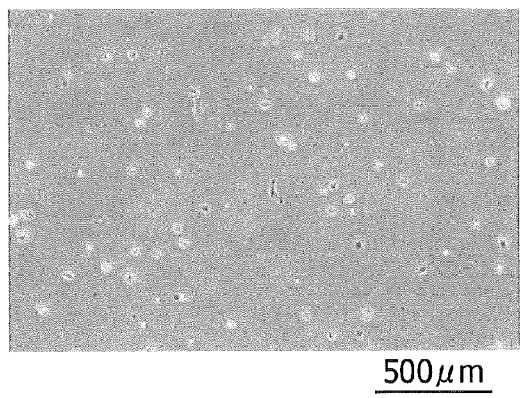
FIG.11B(g) 1 DAY
500μm
FIG.11B(h) 7 DAYS
200μm

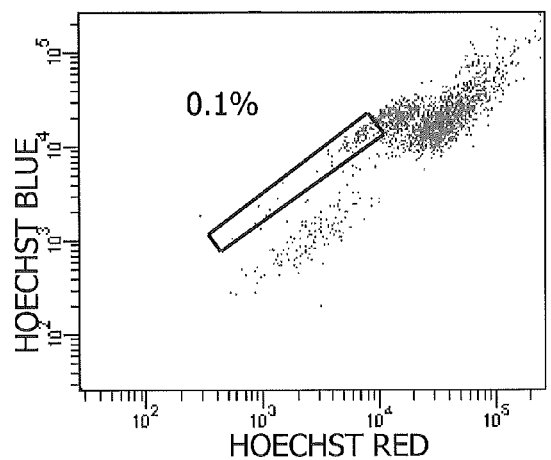
FIG.11C(i)
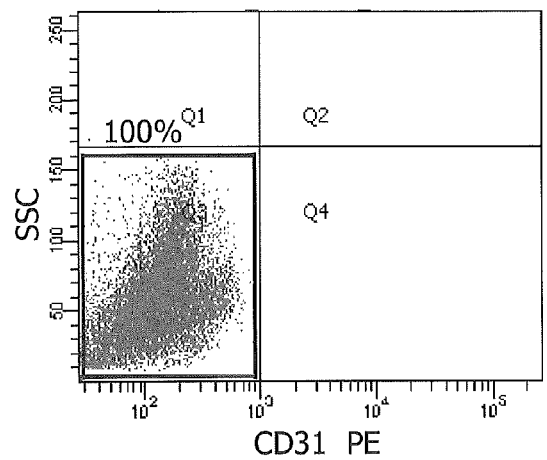
FIG.11C(j)
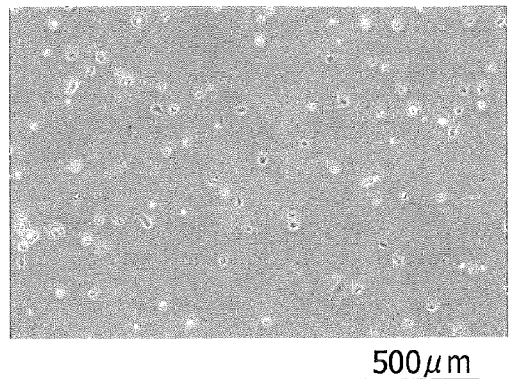
FIG.11C(k) 1 DAY
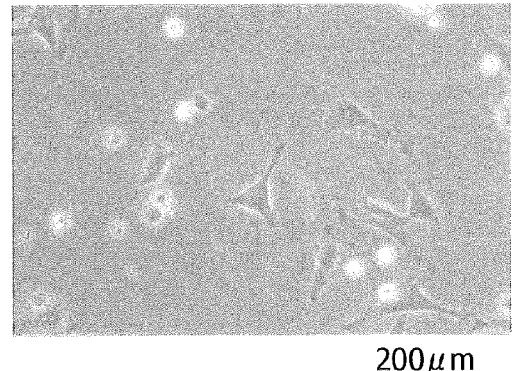
FIG.11C(l) 7 DAYS FIG.12(a) 12HRS 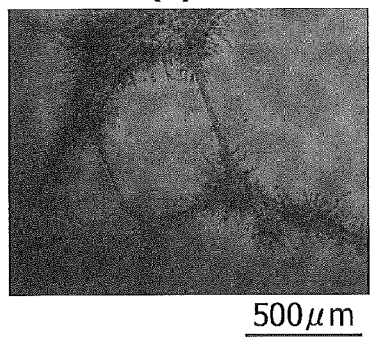 500μm
FIG.12(b) 12HRS 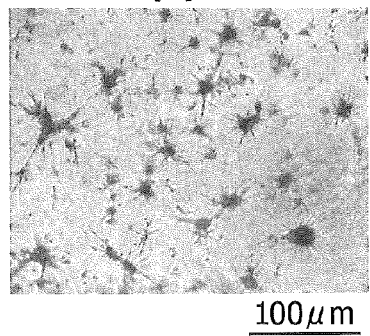 100μm
FIG.12(c) 12HRS 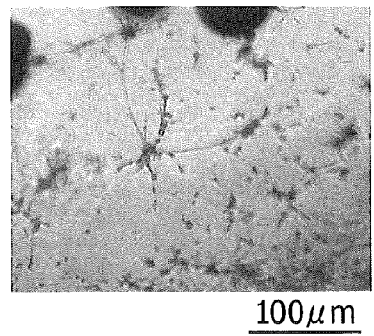 100μm
FIG.12(d) 14DAYS 
FIG.12(e) 14DAYS 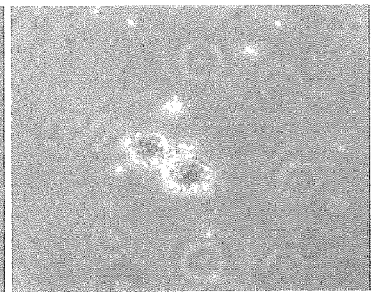
FIG.12(f) 14DAYS 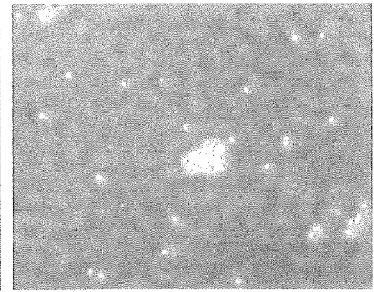

1mm

200μm

100μm

1mm

200μm

100μm

1mm

200μm

100μm

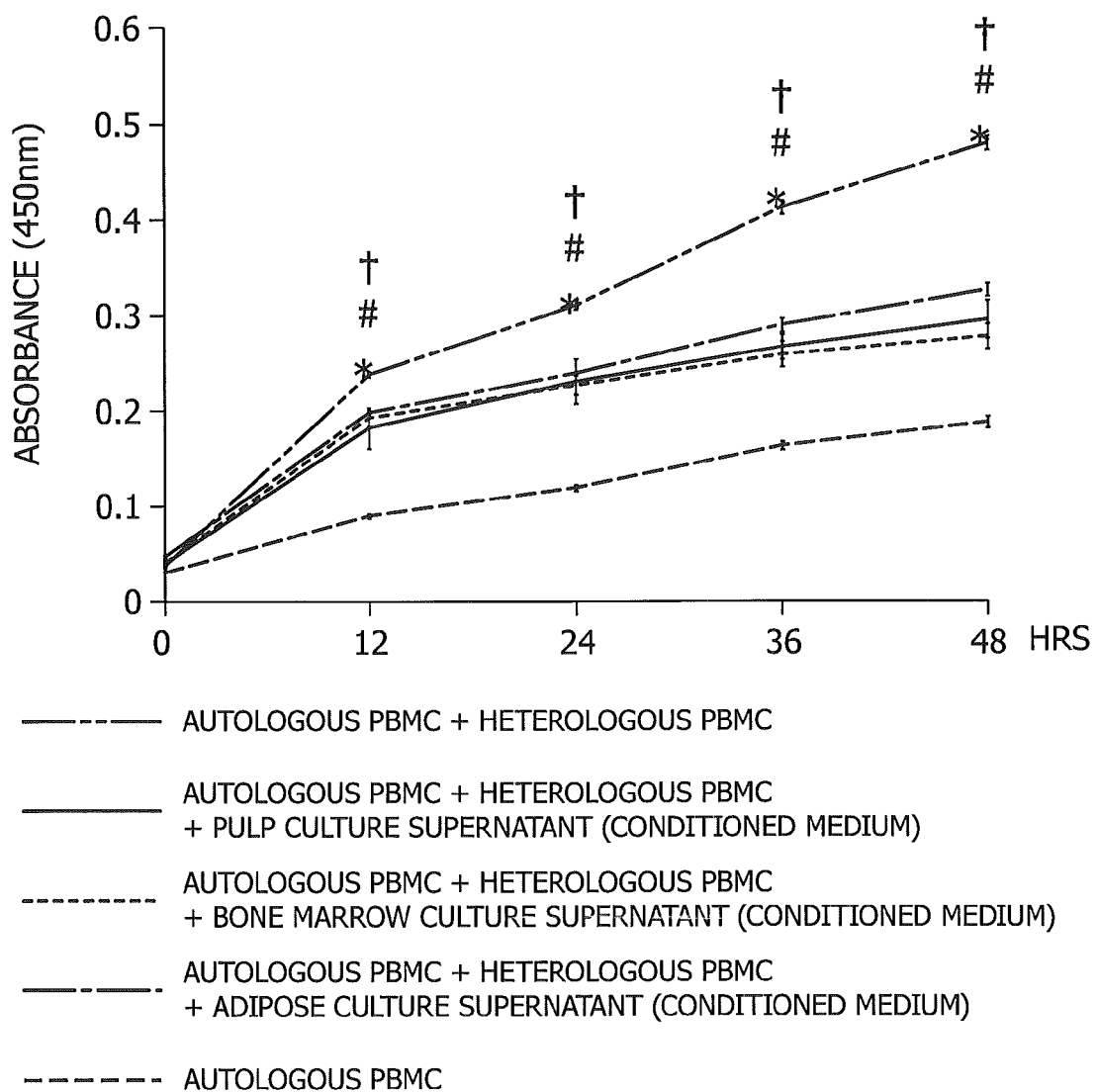

ROOT CANAL FILLING MATERIAL CONTAINING MESENCHYMAL STEM CELLS AND METHOD FOR REGENERATING DENTAL TISSUE USING THE SAME

RELATED APPLICATIONS

This application is a 35 U.S.C. § 371 national stage application of PCT Application No. PCT/JP2012/052155, filed on Jan. 31, 2012, which claims priority from Japanese Application No. 2011-042862, filed on Feb. 28, 2011, the contents of which are incorporated herein by reference in their entireties. The above-referenced PCT International Application was published as International Publication No. WO 2012/117793 A1 on Sep. 7, 2012.

STATEMENT REGARDING ELECTRONIC FILING OF A SEQUENCE LISTING

A Sequence Listing in ASCII text format, submitted under 37 C.F.R. § 1.821, entitled 5576-276TS_ST25.txt, 13,097 bytes in size, generated on Aug. 10, 2013 and filed via EFS-Web, is provided in lieu of a paper copy. This Sequence Listing is hereby incorporated by reference into the specification for its disclosures.

TECHNICAL FIELD

The present invention relates to a root canal filling material containing mesenchymal stem cells and a method for regenerating dental tissue using the same material.

BACKGROUND ART

Currently, caries including tooth fractures constitute about half of the causes of tooth loss, and removal of dental pulp is known to significantly increase the risk of tooth loss. The average lifetime of teeth is said to be 57 years at present. To enable a person to chew with the person's own teeth throughout life, the lifetime of teeth needs to be prolonged by 20 years or more. Despite the "8020" campaign (campaign for promotion of retaining at least 20 of one's own teeth at the age of 80), only 21% of present 80-year old people has achieved the goal. In order to achieve a 50%, a target set by the Japan Dental Association, drastic improvement in caries treatment is necessary.

The removal of dental pulp, i.e., pulp extirpation, causes loss of the reparative dentin forming ability and the defense mechanism against infection and loss of the alarm signal of pain, resulting in an increase in the risk of enlargement of the caries. In addition, there are no perfect methods for pulp extirpation treatment, and after pulp extirpation and root canal filling, a periapical lesion may be caused by leakage of the filler from a tooth crown side; or vertical fracture, aesthetic loss, or postoperative pain may occur.

Accordingly, in the super-aged society, it is very important to develop a new treatment for dental caries and pulpitis by regeneration of dentin and dental pulp incorporating technology of dental regenerative medicine in order to avoid unnecessary extirpation of the pulp and to prolong the lifetime of teeth.

Meanwhile, regarding the dental pulp regeneration, it is hitherto known that the dental pulp of a tooth with an immature root is regenerated by extracting the tooth, extirpating the dental pulp, treating the root canal, and then replanting the tooth. Furthermore, it is reported that even in a tooth with an immature root having a lesion in the apex portion, dental pulp-like tissue is regenerated by extracting the tooth, thoroughly enlarging and cleaning the root canal, and filling the cementum-dentin junction with blood clot, and completely sealing the cavity with mineral trioxide aggregate (MTA).

It is known that the dental pulp-like tissue of a canine healthy tooth with a mature root is regenerated by extracting a tooth, extirpating the pulp, resecting the apex portion or enlarging the apex portion at least 1.1 mm, replanting the tooth, and filling the apex portion with blood clot (Non Patent Literature 1).

Most of reports on the root canal dental pulp regeneration described above focus on teeth with immature roots, and it is not demonstrated that the tissue regenerated in a root canal is dental pulp intrinsic tissue having blood vessels and nerves. In addition, in all cases, teeth are extracted once, enlargement and cleaning of the root canals are performed in vitro, and the root canals are filled with blood clot after replantation.

A method for regenerating dental tissue by extracting a tooth to be treated, extirpating the pulp, and injecting a root canal filling material into the apex side of the root canal is also known, wherein the root canal filling material comprises cells including dental pulp stem cells and an extracellular matrix to which the cells including the dental pulp stem cells adhere (Patent Literature 1).

The dental pulp stem cells are advantageous in that they can be collected from deciduous teeth or wisdom teeth without much burden on patients. However, it is difficult to isolate a sufficient number of dental pulp stem cells from an elderly patient, and actual clinical application is thought to be difficult. Accordingly, in the super-aging society, it is preferable that dental tissue regeneration is realized using a cell source that can be more easily utilized.

CITATION LIST

Patent Literature

[PTL 1] International Publication No. WO2009/113733

Non-Patent Literature

[NPL 1] Laureys et al., Am J Orthod Dentofacial Orthop. 2001 April; 119(4): 335

SUMMARY OF INVENTION

Technical Problem

It is an object of the present invention to provide a root canal filling material for an extracted tooth or a non-extracted tooth, which overcomes the disadvantages of the above-described conventional methods, can be applied to clinical treatment because of its easy availability, and can efficiently enhance dental tissue regeneration, and to provide a method for regenerating dental tissue using the filling material.

Solution to Problem

In order to achieve the above-mentioned object, the present inventors have diligently studied and, as a result, have found that dental pulp can also be regenerated by transplanting any of mesenchymal stem cells excluding dental pulp stem cells, for example, bone marrow stem cells, adipose stem cells, amniotic stem cells, or umbilical cord blood cells, into the root canal of an extracted tooth or a non-extracted tooth, and thus the present invention was accomplished.

An embodiment of the present invention relates to a root canal filling material to be inserted into the apex side of the root canal of an extracted tooth or a non-extracted tooth after pulp extirpation or after root canal enlargement and cleaning of an infected root canal, the root canal filling material comprising mesenchymal stem cells excluding dental pulp stem cells and an extracellular matrix. The mesenchymal stem cells excluding dental pulp stem cells are preferably one of bone marrow stem cells, adipose stem cells, amniotic stem cells, or umbilical cord blood cells.

The mesenchymal stem cells excluding dental pulp stem cells preferably may comprise at least one of SP cells, CD31 negative SP cells, CD24 positive cells, CD29 positive cells, CD44 positive cells, CD73 positive cells, CD90 positive cells, CD105 positive cells, CD31 negative cells, CD45 negative cells, MHC class II negative cells, CD150 positive cells, CXCR4 positive cells, CD271 positive cells, CD133 positive cells, FLK-1 positive cells, CD166 positive cells, and VEGFR2 positive cells.

The root canal filling material preferably further comprises a chemotactic factor comprising at least one of cell migration factors, cell growth factors, and neurotrophic factors. In particular, in the root canal filling material, it is preferable that the mesenchymal stem cells excluding dental pulp stem cells be transplanted or injected into the apex side of the root canal and that the chemotactic factor comprising at least one of cell migration factors, cell growth factors, and neurotrophic factors adheres to the tooth crown side of the root canal.

The cell migration factor may be preferably at least one of SDF1, VEGF, GCSF, SCF, MMP3, Slit, GM-CSF, and serum.

The cell growth factor may be preferably at least one of IGF, bFGF, PDGF, and serum.

The neurotrophic factor may be preferably at least one of GDNF, BDNF, NGF, neuropeptide Y, neurotrophin 3, and serum.

The extracellular matrix may be preferably composed of a biocompatible material comprising at least one of collagen, artificial proteoglycan, gelatin, hydrogel, fibrin, phosphophoryn, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium, and gold.

The content of the mesenchymal stem cells excluding dental pulp stem cells in the extracellular matrix may be preferably equal to or more than $1\times10^3$ cells/μL and equal to or less than $1\times10^6$ cells/μL.

Another aspect of the present invention relates to a method for regenerating dental tissue by a tooth extracting or tooth non-extracting process. The method may comprise a step of injecting any one of root canal filling materials described above into the apex side of a root canal after pulp extirpation or after root canal enlargement and cleaning of an infected root canal.

The method preferably may further comprise a step of enlarging the root canal such that the diameter of the root canal of the apex portion is increased to a predetermined size, before the step of injecting the root canal filling material into the apex side of the root canal.

Another aspect of the present invention relates to a method of ectopically regenerating dental tissue. The method may comprise steps of extirpating the pulp of a tooth of a first individual, cutting out a predetermined length of the root portion of the tooth, sealing one end of the root canal subjected to the pulp extirpation, injecting a root canal filling material containing mesenchymal stem cells and an extracellular matrix into the root canal, and transplanting the root injected with the filling material into a second individual, and also preferably comprises a step of replanting the root in which dental pulp has been regenerated into an alveolar bone.

Advantageous Effects of Invention

The root canal filling material and the method for regenerating dental tissue using the filling material according to the present invention can enhance the regeneration of dental tissue by a tooth extracting or a tooth non-extracting processes. In dental tissue regeneration by the root canal filling material and the method for regenerating dental tissue using the filling material, internal resorption and external resorption are not observed in the regenerated tissue, and also odontoclasts are not observed, and regenerated tissue in which odontoblasts are smoothly arranged on the dentin wall can be provided. In addition, the method for ectopically regenerating dental tissue according to the present invention is useful in, for example, that dental tissue can be regenerated in a heterogeneous individual such as a pig carrying a human gene (humanized pig) considering immunological rejection. They are very promising in dental treatment in the super-aging society.

BRIEF DESCRIPTION OF DRAWINGS

FIG. 4 includes explanatory diagrams of illustrating root canal filling materials according to a second embodiment, wherein diagram (a) shows a configuration for allowing a chemotactic factor to adhere to the tooth crown side of a root canal, and diagram (b) shows a configuration for leaving an extracellular matrix on the tooth crown portion side.

FIG. 5 is an explanatory diagram of illustrating a process of producing the root canal filling material according to the second embodiment.

FIG. 7A(b) shows further isolation of a different fraction from the dental pulp tissue using an antibody against CD31;

FIG. 7A(c) shows a phase contrast microscopic image of primary CD31$^-$ SP cells derived from canine dental pulp tissue on the third day; and FIG. 7A(d) shows that of the cells on the tenth day. The experiments were each repeated 12 times, and typical experimental results are shown.

FIG. 7B(f) shows further isolation of a different fraction from the bone marrow tissue using an antibody against CD31;

FIG. 7B(g) shows a phase contrast microscopic image of primary CD31$^-$ SP cells derived from canine bone marrow tissue on the third day; and FIG. 7(h) shows that of the cells on the tenth day.

FIG. 7C shows isolation of CD31$^-$ SP cells derived from canine adipose tissue, wherein FIG. 7C(i) shows the results of flow cytometric analysis; FIG. 7C(j) shows further isolation of a different fraction from the adipose tissue using an antibody against CD31; FIG. 7C(k) shows a phase contrast microscopic image of primary CD31$^-$ SP cells derived from canine bone marrow tissue on the third day; and FIG. 7C(l) shows that of the cells on the tenth day.

FIG. 8 includes phase contrast microscopic images showing multilineage potentials of CD31$^-$ SP cells derived from canine dental pulp tissue (a), (d), and (g); canine bone marrow tissue (b), (e), and (h); and canine adipose tissue (c), (f), and (i), wherein (a), (b), and (c) show the endothelial differentiation potentials in matrigel assay on 12 hours after seeding; (d), (e), and (f) show the neurosphere formation on the 14th day after induction of cell populations of the fourth passage; (g), (h), and (i) show the results on the 14th day after neuronal induction by dissociation of the neurospheres; and (j) shows expression of mRNAs of neurofilament and neuromodulin. The experiment was repeated three times, and one representative experiment is presented.

FIG. 10A shows complete regeneration of dental pulp tissue in autologous transplantation of a filling material according to the present invention into a canine root canal after pulp extirpation, wherein (a), (d), and (g) are microscopic images when canine dental pulp CD31$^-$ SP was transplanted; (b), (e), and (h) are those when canine bone marrow CD31$^-$ SP was transplanted; and (c), (f), and (i) are those when canine adipose CD31$^-$ SP was transplanted, wherein (a) to (f) are those taken on the 14th day after transplantation; and (g) to (i) are those taken on the 28th day after transplantation. In the images, matrix formation is indicated by the arrows, and calcified tissue is indicated by m. The graph (j) shows proportions of areas of newly regenerated tissue to the area of the root canal on the 14th day. The data are shown as mean±standard deviation.

FIG. 11A shows isolation of CD31$^-$ SP cells derived from pig dental pulp tissue, wherein (a) shows the results of flow cytometry analysis; (b) shows further isolation of a different fraction from the dental pulp tissue using an antibody against CD31; (c) shows a phase contrast microscopic image of primary CD31$^-$ SP cells derived from pig dental pulp tissue on the third day; and (d) shows that of the cells on the seventh day. The experiments were each repeated 12 times, and one representative experiment is presented.

FIG. 11B shows isolation of CD31$^-$ SP cells derived from pig bone marrow tissue, wherein (e) shows the results of flow cytometric analysis; (f) shows further isolation of a different fraction from the bone marrow tissue using an antibody against CD31; (g) shows a phase contrast microscopic image of primary CD31$^-$ SP cells derived from pig bone marrow tissue on the third day; and (h) shows that of the cells on the seventh day.

FIG. 11C shows isolation of CD31$^-$ SP cells derived from pig adipose tissue, wherein (i) shows the results of flow cytometric analysis; (j) shows further isolation of a different fraction from the adipose tissue using an antibody against CD31; (k) shows a phase contrast microscopic image of primary CD31$^-$ SP cells derived from pig bone marrow tissue on the third day; and (l) shows that of the cells on the seventh day.

FIG. 12 includes phase contrast microscopic images showing multi-lineage differentiation potentials of CD31$^-$ SP cells derived from pig dental pulp tissue (a) and (d); pig bone marrow tissue (b) and (e); and pig adipose tissue (c) and (f), wherein (a), (b), and (c) show endothelial differentiation potentials in matrigel assay on 12 hours after seeding; and (d), (e), and (f) show neurosphere on the 14th day after induction of cell populations of the fourth passage. The experiment was repeated three times, and one representative experiment is presented.

FIG. 15 shows investigation of immunosuppression by conditioned medium of canine dental pulp, bone marrow, and adipose in use of canine autologous and allogenic PBMCs (peripheral blood mononuclear cells), *: P<0.001, dental pulp vs. bone marrow, #: P<0.001, dental pulp vs. adipose, †: P<0.001, bone marrow vs. adipose.

DESCRIPTION OF EMBODIMENTS

The present invention will now be described in detail with reference to the drawings. The present invention is not limited to the description below.

First Embodiment

Figure 1:
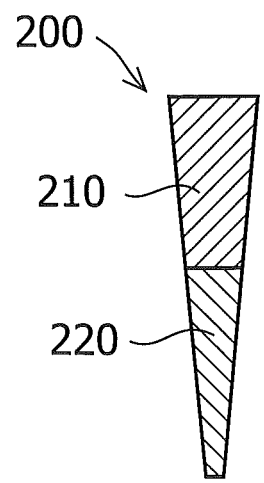
FIG. 1 is an explanatory diagram of a root canal filling material according to a first embodiment.

In accordance with a first embodiment, the present invention relates to a root canal filling material containing an extracellular matrix and mesenchymal stem cells excluding dental pulp stem cells. FIG. 1 is an explanatory diagram of a root canal filling material 200 according to the present embodiment. The root canal filling material 200 is formed by attaching mesenchymal stem cells 220 excluding dental pulp stem cells to an extracellular matrix 210. Herein, the term "formed by attaching" means that when the extracellular matrix is, for example, liquid or fluid, mesenchymal stem cells excluding dental pulp stem cells are mixed, preferably uniformly, with the extracellular matrix, whereas when the extracellular matrix is in a form having a certain shape such as a three-dimensional sponge-like structure described below, mesenchymal stem cells excluding dental pulp stem cells are incorporated in and held, preferably uniformly, on and inside the structure composed of the extracellular matrix. The mesenchymal stem cells 220 excluding dental pulp stem cells are attached to the root canal filling material 200 in the apical side of the root canal. Herein, the phrase "attached to the root canal filling material 200 in the apical side of the root canal" means that a root canal filling material is formed such that mesenchymal stem cells excluding dental pulp stem cells are injected into the apical side of a root canal and are transplanted thereinto.

The mesenchymal stem cells excluding dental pulp stem cells may be derived from any tissue excluding dental pulp. For example, bone marrow stem cells, adipose stem cells, amniotic stem cells, or umbilical blood stem cells can be used. In addition, these mesenchymal stem cells may be autologous cells extracted from tissue of an individual itself as a subject to be treated by dental tissue regeneration or may be homogeneous cells extracted from tissue of an individual other than the subject individual to be treated by dental tissue regeneration. The subject to be treated with dental tissue regeneration may be a mammal, in particular, a human.

The bone marrow stem cell which is an example of mesenchymal stem cells excluding the dental pulp stem cell is a stem cell derived from bone marrow and can be extracted and isolated from bone marrow tissue by a known method. Similarly, the adipose stem cell, the amniotic stem cell, and the umbilical blood stem cell are also stem cells respectively derived from adipose tissue, amnionic tissue, and umbilical blood tissue and can be extracted and isolated from the respective tissues by known methods.

As the mesenchymal stem cells excluding dental pulp stem cells, SP cells and/or an isolated cellular fraction expressing a specific cell marker may be used. Specifically, the mesenchymal stem cells excluding dental pulp stem cells can include at least one of CD29 positive cells, CD44 positive cells, CD73 positive cells, CD90 positive cells, CD105 positive cells, CXCR4 positive cells, CD31 negative cells, CD45 negative cells, MHC class II negative cells, CD150 positive cells, CXCR4 positive cells, CD271 positive cells, CD133 positive cells, FLK-1 positive cells, CD166 positive cells, and VEGFR2 positive cells. Throughout the specification, positive may be referred to as "+", and negative may be referred to as "−".

In particular, the mesenchymal stem cells preferably include CD31 negative side population (SP) cells. Throughout the specification, CD31 negative side population cells are also referred to as CD31⁻ SP cells. CD31⁻ SP cells transplanted into an ischemic lesion of a mouse lower limb enhance blood flow recovery and angiogenesis, and CD31⁻ SP cells transplanted into an ischemic lesion of a rat cerebral infarction enhance differentiation to nerve cells and allow recovery from motor paralysis. In addition, transplantation of CD31⁻ SP cells into an amputated section of a canine vital dental pulp causes angiogenesis, nerve regeneration, and dental pulp regeneration in the cavity of the amputated section of the vital dental pulp. It is believed that the dental pulp-regenerating potential of CD31⁻ SP cells as mesenchymal stem cells is high.

The SP cells can be isolated by a common method known to those skilled in the art, cell sorting utilizing flow cytometry. A cellular fraction expressing a specific cell marker can be isolated by flow cytometry or a magnetic bead method using an antibody. It is preferable to further culture the isolated fraction and use the mesenchymal stem cells cultured to the third to fifth passages as the root canal filling material according to this embodiment.

The content of the mesenchymal stem cells in the root canal filling material 200 is preferably $1\times10^3$ cells/μL or more and $1\times10^6$ cells/μL or less. A content of the mesenchymal stem cells less than $1\times10^3$ cells/μL may cause insufficient regeneration of dental tissue in the root canal, whereas a content of the mesenchymal stem cells more than $1\times10^6$ cells/μL may cause an unexpected side effect on the target tooth.

The extracellular matrix (scaffold) 210 is preferably composed of a biocompatible material comprising at least one of collagen, artificial proteoglycan, gelatin, hydrogel, fibrin, phosphophoryn, heparan sulfate, heparin, laminin, fibronectin, alginic acid, hyaluronic acid, chitin, PLA (polylactic acid), PLGA (poly (lactic-glycolic) acid copolymer), PEG (polyethylene glycol), PGA (polyglycolic acid), PDLLA (poly-DL-lactic acid), PCL (polycaprolactone), hydroxyapatite, β-TCP, calcium carbonate, titanium, and gold. The proteoglycan is one of glycoconjugates in which a protein and a sugar chain (glycosaminoglycan) are covalently bonded to each other. In addition, as the extracellular matrix, a three-dimensional sponge-like structure composed of nanofibers having a number average diameter of 1 nm to 1000 nm produced from a polymer such as a thermoplastic polymer can also be used. Such a three-dimensional structure preferably has a porosity of 80% to 99.99%.

The collagen used as the extracellular matrix is preferably a type I/type III collagen mixture, a mixture of type I collagen and type III collagen. Type I collagen is basic collagen and is fibrous collagen. Type III collagen can form a fine net-like structure called reticular fibers, different from the collagen fibers, to form a scaffold for cells, for example.

In the case of using the above-described collagen mixture, the proportion of the type III collagen is preferably 10% by weight or more and 50% by weight or less. In a proportion of type III collagen of greater than 50% by weight, the collagen mixture may not be solidified. In contrast, a proportion of type III collagen of less than 10% by weight makes the proportion of type I collagen high and may cause regeneration of dentin instead of angiogenesis as described below.

Figure 2:
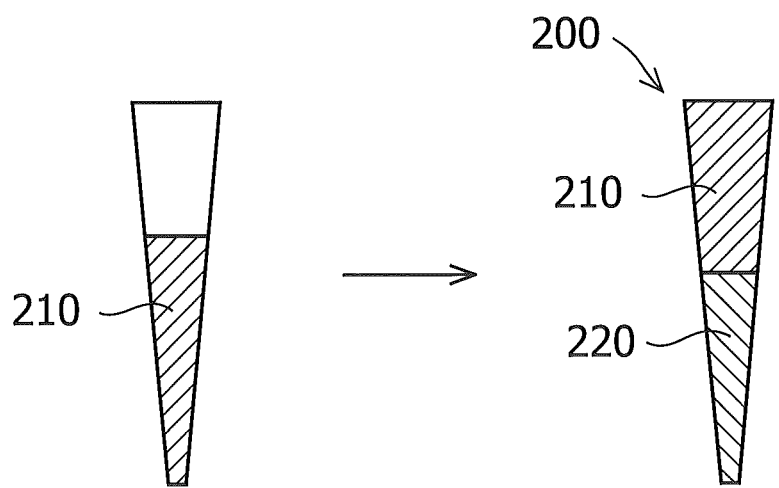
FIG. 2 includes explanatory diagrams of illustrating a process of producing the root canal filling material according to the first embodiment.

A method of producing the root canal filling material 200 according to this embodiment will now be described with reference to FIG. 2.

The root canal filling material 200 is formed by attaching mesenchymal stem cells 220 excluding dental pulp stem cells to the apical side of an extracellular matrix 210. The mesenchymal stem cells 220 are desirably adhered to ¼ to ⅔ of the apical portion of the root canal filling material 200, more desirably ⅓ of the apical portion. In the case of using an extracellular matrix in a fluid state, the root canal filling material can be formed by preparing a first composition containing an extracellular matrix and mesenchymal stem cells and a second composition containing an extracellular matrix such that the first composition and the second composition are located at the apical portion and the tooth crown portion, respectively. In a specific example of the producing method, 10 µL to 13 µL of a type I/type III collagen mixture and then 7 µL to 10 µL of a type I/type III collagen mixture (e.g., Collagen XYZ (Nitta Gelatin Inc.)) containing mesenchymal stem cells excluding dental pulp stem cells can be suctioned with, for example, a Pipetman tip such that the total amount is 20 µL. The suction with a Pipetman tip or the like is preferably slowly performed so as not to cause occurrence of air bubbles. When air bubbles occur inside the root canal filling material, the air bubbles may prevent migration of the cells and thereby inhibit the induction of dental tissue regeneration. A Pipetman tip having a smaller inner diameter is preferred, and, for example, one having an inner diameter of 0.5 to 0.7 mm at the bottom of the tip can be used. For example, a microcapillary tip, H-010-96RS, from QSP may be used. The shape of the root canal filling material is not specifically limited, and may be, for example, a cone, a truncated cone, or a cylinder. Alternatively, in the case of using an extracellular matrix in a three-dimensional sponge-like structure, the root canal filling material can be prepared by absorbing mesenchymal stem cells excluding dental pulp stem cells in the apical portion of a structure containing an extracellular matrix formed in a size conformable to a root. The volume of the extracellular matrix used in the description of this embodiment is merely an example, and the filling material is not limited to a specific volume and can be appropriately determined depending on the volume of a root canal of a tooth of which dental pulp is regenerated.

A method for regenerating dental tissue by a tooth non-extracting procedure using a root canal filling material 200 will now be described as an example of a method for regenerating dental tissue, with reference to FIGS. 3A to 3F.

Figure 3A:
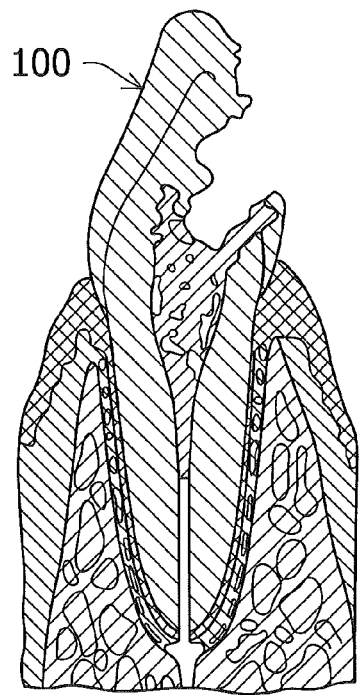
FIG. 3A is an explanatory diagram of a tooth suffering from pulpitis.

As shown in FIG. 3A, the method for regenerating dental pulp tissue according to this embodiment regenerates dental tissue in, for example, a subject with pulpitis, the target tooth 100, in a non-extracted state. The tooth as a subject refers to a tooth in which bacterial infection reaches the crown dental pulp or root dental pulp by caries or pulpitis, for example.

Figure 3B:
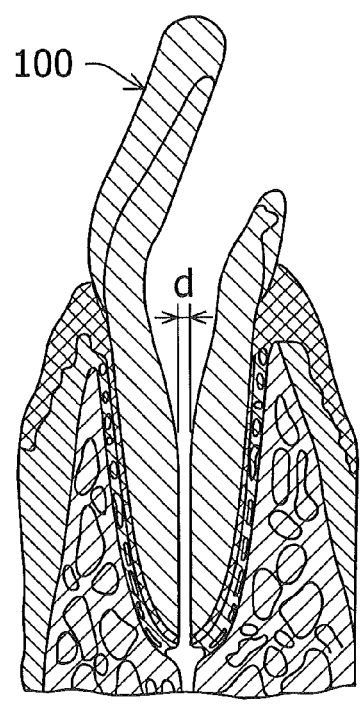
FIG. 3B is a schematic diagram illustrating enlargement treatment of the root canal after pulp extirpation.

As shown in FIG. 3B, the target tooth 100 as a subject is subjected to pulp extirpation or to root canal enlargement and cleaning of the infected root canal. The term "pulp extirpation" means that the dental pulp present inside a tooth is removed. The pulp extirpation can be performed by a general method known to those skilled in the art, for example, by a method performing mechanical enlargement with a hand or electric powered reamer/file or a rotary engine and then washing with sodium hypochlorite and oxydol alternately. The term "infected root canal" refers to a root canal in which bacteria reach the dental pulp and then the dentin of the root canal wall. The term "after enlargement and cleaning of the root canal" refers to after removal of bacteria from the infected root canal. Bacteria can be removed by, for example, applying a drug to the inside of the root canal after alternately washing.

After pulp extirpation, the root canal of the target tooth is enlarged, and the root canal at the apex portion is desirably enlarged to a predetermined diameter. The enlargement of the root canal allows the root canal subjected to pulp extirpation or to infection root canal treatment to be easily filled with the root canal filling material 200. In addition, the enlargement enhances approaches of blood vessels and nerves from periapical tissue. Herein, the term "apex" refers to the end of a target tooth and being connected to the alveolar bone (the end portion of the root). The enlargement of the root canal of a tooth can be performed by a mechanical method by hand or an electric powered reamer/file or a rotary motor.

For example, in FIG. 3B, the diameter, d, of the root canal at the apex portion is desirably 0.6 mm or more and 1.5 mm or less. If the diameter, d, of the root canal is smaller than 0.6 mm, approach of blood vessels and nerves from periapical tissue may hardly occur, and filling with the root canal filling material 200 may also be difficult. In contrast, if the diameter of the root canal is greater than 1.5 mm, an excessive burden is imposed on the target tooth, which burden may easily cause cracking in the tooth.

Figure 3C:
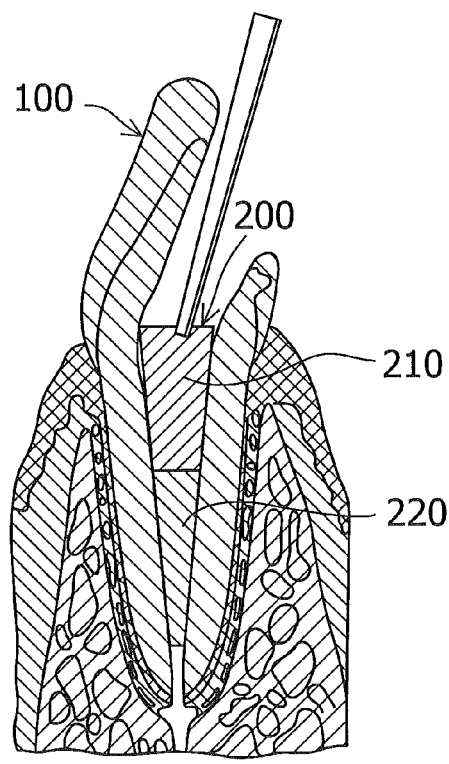
FIG. 3C is a schematic diagram illustrating filling with a root canal filling material.

Then, as shown in FIG. 3C, the apical side of the root canal is filled with the root canal filling material 200 using tweezers, for example. The root canal filling material 200 contains a biological material and can therefore be a biological root canal filling material. The root canal filling material 200 desirably fills the space corresponding to the portion where the dental pulp has been present in the root canal. If the extracellular matrix 210 is in a gel form, the root canal filling material 200 cannot be pinched with tweezers or the like, but can be injected with a Pipetman or by injection, for example.

Figure 3D:
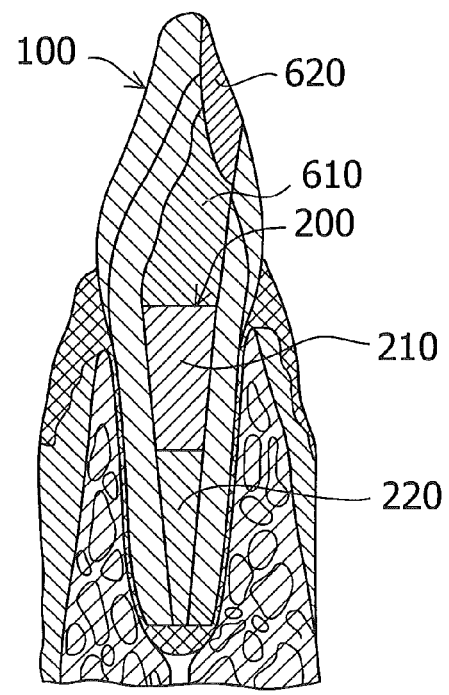
FIG. 3D is a schematic diagram illustrating injection of Spongel (gelatin) and resin.

After injection of the root canal filling material 200 into the apical side of the root canal, as shown in FIG. 3D, gelatin 610 is injected on the root canal filling material 200, followed by covering with resin 620. The gelatin and the resin are not specifically limited, and those that are commonly used in dental treatment can be used.

Figure 3E:
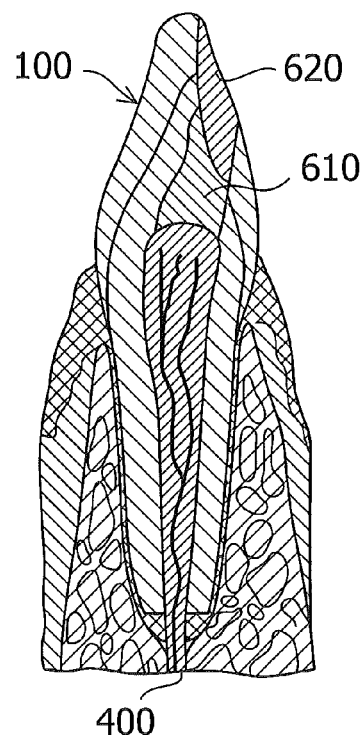
FIG. 3E is a schematic diagram illustrating dental pulp regeneration and vasculogenesis/angiogenesis.

As a result, dental tissue in the root canal is regenerated. As shown in FIG. 3E, examples of the dental tissue to be regenerated include tissue inherent to dental pulp, blood vessels 400, and nerves in the root canal. In addition, in the case of using a morphogenetic factor such as BMPs, examples of the dental tissue to be regenerated include dentin. Furthermore, in the case of filling an infected root canal with the root canal filling material 200, examples of the dental tissue to be regenerated include periodontal tissue such as periodontal ligament (periodontal tissue for planting a tooth in an alveolar bone) and cementum.

Figure 3F:
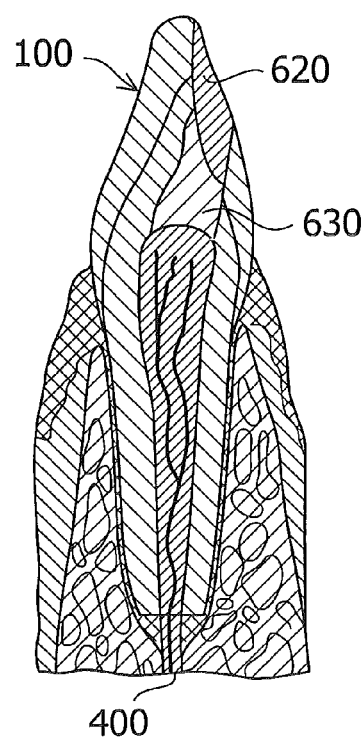
FIG. 3F is a schematic diagram illustrating injection of a morphogenetic factor and resin.
Figure 3G:
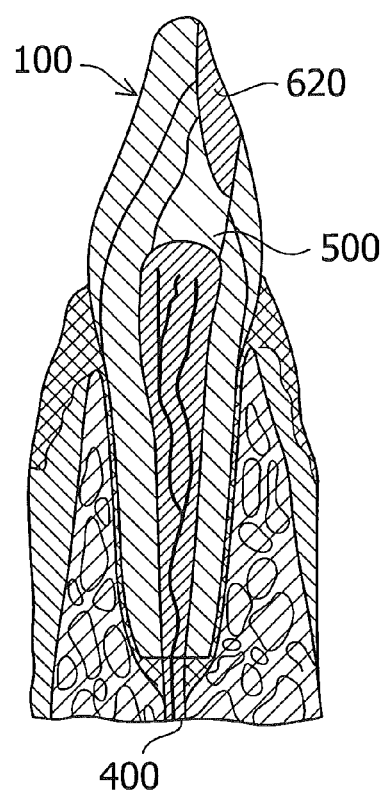
FIG. 3G is a schematic diagram illustrating dentin regeneration.

Subsequently, the resin 620 is removed once, and as shown in FIG. 3F, a morphogenetic factor 630 such as BMPs or a dentin forming factor is applied to the dental pulp at the tooth crown portion, followed by covering with resin 620. The application of the morphogenetic factor 630 or the dentin forming factor to the dental pulp at the tooth crown portion also allows regeneration of dentin 500, as shown in FIG. 3G.

Furthermore, in regeneration of dental tissue using the root canal filling material 200 according to this embodiment, internal resorption and external resorption are not recognized in the regenerated tissue, and also odontoclasts are not observed, and odontoblasts are smoothly arranged on the dentin wall. In addition, though the presence of a large amount of blood clots due to bleeding is thought to disturb the regeneration of dental pulp tissue, the non-tooth extraction process can suppress occurrence of blood clots and thereby has an advantage of efficiently inducing regeneration of dental tissue. In addition, medical application to the root canal allows postponement of filling of the root canal until disappearance of bleeding and symptoms after root canal enlargement, which procedure has an advantage of approaching to actual clinical treatment.

Figure 3H:
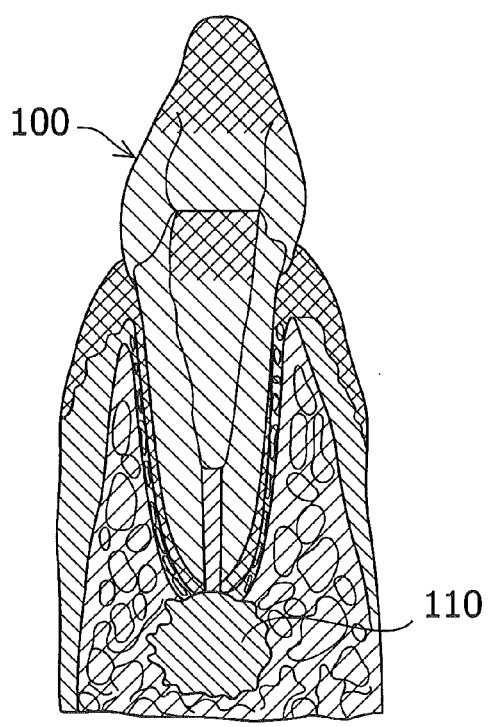
FIG. 3H is a schematic diagram showing apical periodontitis in which bacteria reach the dentin of the root canal wall and further the periapical tissue.

As described above, the target tooth 100 may be a tooth having a bacterial infection reaching the crown dental pulp or root dental pulp by caries, pulpitis, etc., but is not limited thereto. That is, examples of the target tooth 100 include teeth having a reduced neurological function to weaken the occlusion sense. In such cases, the occlusion sense can be enhanced by regenerating dental pulp through filling of the root canal with the root canal filling material 200 after pulp extirpation. In addition, as shown in FIG. 3H, examples of the tooth 100 as a subject include teeth in which bacterial infection reaches the periapical tissue (teeth in which bacteria reach the dental pulp and then further reach the dentin of the root canal wall and the periapical tissue). Many of these teeth involve apical periodontitis 110. The injection of the root canal filling material 200 is preferably performed after root canal enlargement and cleaning of the infected root canal.

Figure 3I:
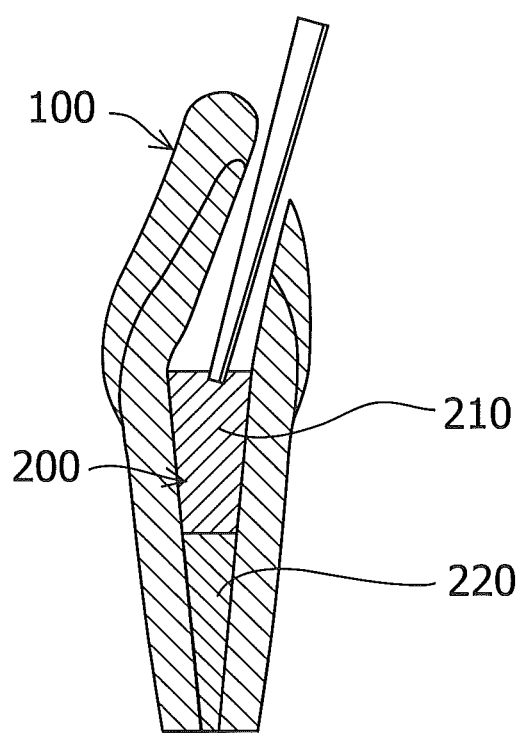
FIG. 3I is a schematic diagram illustrating filling the root canal with a root canal filling material, wherein an extracted tooth is subjected to pulp extirpation and sterilization, and the apex portion is cut to form an opening.

The root canal filling material according to this embodiment can also be used in an extracted tooth as in the non-extracted tooth. In the case of using in an extracted tooth, first, the subject desired to be subjected to dental tissue regeneration is extracted. After tooth extraction, and root canal enlargement and cleaning of the infected root canal, pulp extirpation and sterilization are performed. The pulp extirpation and sterilization can be performed as in the method described in the above non-tooth extraction process. Subsequently, the apex portion is cut to form an opening, and the root canal filling material is transplanted thereinto. The cutting position of the apex portion is preferably 1 mm to 2 mm from the lower end. The cutting of the apex portion can be performed by a common dental method, for example, with an air turbine or electric engine. The injection of the root canal filling material can be performed as in the method described in the above non-tooth extraction process. FIG. 3I shows filling the apical side of the root canal of a tooth in an extracted state with the root canal filling material 200. After injection of the root canal filling material, gelatin is injected on the root canal filling material, followed by covering with resin. Subsequently, the extracted tooth can be replanted into the socket (odontectomized cavity). The tooth in the extracted state has advantages, in particular, that the affected tooth can be treated under direct sight and that damage of periapical tissue is low.

Second Embodiment

The root canal filling material according to a second embodiment contains mesenchymal stem cells excluding dental pulp stem cells and a chemotactic factor. The chemotactic factor includes at least one of cell migration factors, cell growth factors, and neurotrophic factors.

FIGS. 4(a) and (b) are explanatory diagrams illustrating root canal filling materials 200 according to the second embodiment of the present invention. In the root canal filling material 200 shown in FIG. 4(a), mesenchymal stem cells 220 excluding dental pulp stem cells are attached to the apex side of the root canal, and a chemotactic factor 230 including at least one of cell migration factors, cell growth factors, and neurotrophic factors is attached to the tooth crown side of the root canal (e.g., ½ to ⅔ of the root canal in upper side).

Even if the mesenchymal stem cells 220 are attached to the tooth crown side of the root canal, the cells are not supplied with nutrition from the tissue, which may cause necrosis of the cells. Accordingly, the mesenchymal stem cells 220 are attached to the apical side of the root canal, and the chemotactic factor 230 is attached to the tooth crown side of the root canal. In addition, the mesenchymal stem cells 220 adhering to the apical side of the root canal are attracted by the chemotactic factor adhering to the tooth crown side of the root canal to readily enhance dental tissue regeneration. In addition, as shown in FIG. 4(b), it is also possible to retain the extracellular matrix 210 on the tooth crown side of the root canal of the root canal filling material 200.

The chemotactic factor may include one of cell migration factors, cell growth factors, and neurotrophic factors or a combination of two or more thereof.

The cell migration factor is a molecule that activates a signaling system involved in migration of cells by binding to a receptor. The cell growth factor is a molecule that activates a signaling system involved in growth of cells by binding to a receptor. The neurotrophic factor is a molecule that activates a signaling system involved in survival of cells by binding to a receptor.

The cell migration factor is preferably at least one of SDF1, VEGF, GCSF, SCF, MMP3, Slit, GM-CSF, and serum. In particular, MMP3 shows high chemotaxis and can therefore be preferably used.

The cell growth factor is preferably at least one of IGF, bFGF, PDGF, and serum.

The neurotrophic factor is preferably at least one of GDNF, BDNF, NGF, neuropeptide Y, neurotrophin 3, and serum. The serum is preferably autoserum. The autoserum is the serum of an individual to be subjected to dental tissue regeneration and can be prepared by leaving fresh blood to stand for 30 minutes and then collecting the supernatant by centrifugation.

The content of the chemotactic factor in the extracellular matrix to which the chemotactic factor adheres is preferably 0.1 ng/µL or more and 500 ng/µL or less. A content of the chemotactic factor of less than 0.1 ng/µL may cause a low degree of migration, whereas a content of the chemotactic factor of higher than 500 ng/µL may cause an unexpected side effect on the target tooth 100.

With reference to FIG. 5, a method of producing the root canal filling material 200 according to this embodiment will now be described. FIG. 5 is an explanatory diagram of illustrating a process of producing the root canal filling material 200 by attaching a chemotactic factor 230 to the tooth crown side of the root canal.

In the root canal filling material 200 according to the second embodiment, in the case of using an extracellular matrix in a fluid state, a first composition containing an extracellular matrix and mesenchymal stem cells excluding dental pulp stem cells and a second composition containing an extracellular matrix and a chemotactic factor are prepared, and these compositions can be injected and transplanted such that the first composition and the second composition are located at the apical portion and the tooth crown portion, respectively. In a specific example of the producing method, 10 μL to 13 μL of a type I/type III collagen mixture (the mixing ratio of type I collagen and type III collagen is 1:1) containing a chemotactic factor and then 7 μL to 10 μL of a type I/type III collagen mixture containing mesenchymal stem cells are suctioned with, for example, a Pipetman tip such that the total amount is 20 μL. In also the second embodiment, the suction with a Pipetman tip etc. is preferably slowly performed not to cause the occurrence of air bubbles. A Pipetman tip having a smaller inner diameter is preferred. Thus, the root canal filling material 200 shown in FIG. 4(a) is produced.

The root canal filling material 200 according to the second embodiment can be used as in the first embodiment, i.e., the apical side of the root canal is filled with the filling material after pulp extirpation or after root canal enlargement and cleaning of the infected root canal of a tooth without extraction or with extraction and apicoectomy in which the apex portion is cut to form an opening.

Since the root canal filling material 200 according to this embodiment contains a chemotactic factor, dental tissue regeneration can be further efficiently achieved, and in the regenerated tissue, internal resorption does not occur, odontoclasts are not observed, and odontoblasts are smoothly arranged on the dentin wall.

Third Embodiment

In the above first embodiment, the root canal filling material 200 is constituted by mesenchymal stem cells 220, excluding dental pulp stem cells, adhering to the apex side of the root canal of the root canal filling material 200. However, the filling material is not limited to such embodiments, and the mesenchymal stem cells 220 may be uniformly mixed with the entire root canal filling material 200. Such a root canal filling material 200 can also be used for both teeth in an extracted state and a non-extracted state, and the use thereof allows regeneration of dental tissue, in a tooth with a mature root, in which internal resorption does not occur, odontoclasts are not observed, and odontoblasts are smoothly arranged on the dentin wall. Such a root canal filling material 200 is produced by, for example, uniformly mixing the mesenchymal stem cells 220 and a type I/type III collagen mixture, which is an example of the extracellular matrix, with avoiding occurrence of air bubbles.

In the above second embodiment, the root canal filling material 200 is constituted by mesenchymal stem cells 220, excluding dental pulp stem cells, adhering to the apex side of the root canal and also a chemotactic factor 230 adhering to the tooth crown side of the root canal. However, the filling material is not limited to such embodiments, and both the mesenchymal stem cells 220 and the chemotactic factor 230 may be uniformly mixed with the entire root canal filling material 200. Such a root canal filling material 200 can also be used for both teeth in an extracted state and a non-extracted state. The use thereof allows regeneration of dental tissue in a tooth with a mature root, in which internal resorption does not occur, odontoclasts are not observed, and odontoblasts are smoothly arranged on the dentin wall. This root canal filling material 200 is produced by, for example, uniformly mixing the mesenchymal stem cells, the chemotactic factor, and a type I/type III collagen mixture which is an example of the extracellular matrix, with avoiding occurrence of air bubbles.

Fourth Embodiment

A fourth embodiment of the present invention relates to a method of ectopically regenerating dental tissue using the root canal filling material described in the above first to third embodiments. The method of ectopically regenerating dental tissue includes steps of extirpating the pulp of a tooth of a first individual, cutting out a predetermined length of the root portion of the tooth, injecting the root canal filling material into the root canal, and transplanting the root injected with the filling material into a second individual.

The root canal filling material may be those described in the above first to third embodiments. Furthermore, dental pulp stem cells can also be used in place of the mesenchymal stem cells constituting the root canal filling materials in the above first to third embodiments. In such a case, the dental pulp stem cells preferably include a dental pulp CXCR4 positive cell, a SSEA-4 positive cell, a FLK-1 positive cell, a CD105 positive cell, a dental pulp SP cell, a CD31 negative and CD146 negative cell, a CD24 positive cell, a CD150 positive cell, and a CD73 positive cell and at least one of a CD271 positive cell and a CD166 positive cell; and the dental pulp SP cell preferably includes at least one of a CXCR4 positive, SSEA-4 positive, FLK-1 positive, CD31 negative and CD146 negative, CD24 positive, CD105 positive, CD150 positive, CD73 positive, or CD271 positive cell and a CD166 positive cell.

The above first individual is an individual desired to be subjected to tooth regeneration and is preferably a mammal and is typically a human. The above second individual is different from the first individual and is a mammal other than a human. The second individual, for example, may be a mouse or a pig, and an immunodeficient mouse or pig can be used.

Figure 6A:
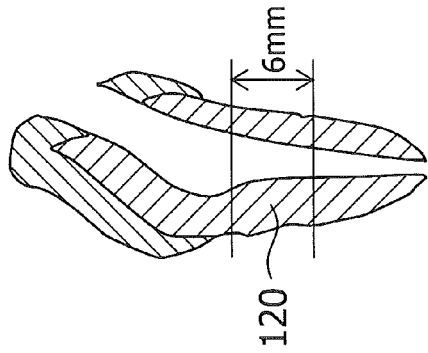
FIG. 6 includes schematic diagrams illustrating a method of ectopically regenerating dental tissue by transplanting the root injected with a filling material into an immunodeficient mouse.
Figure 6B:
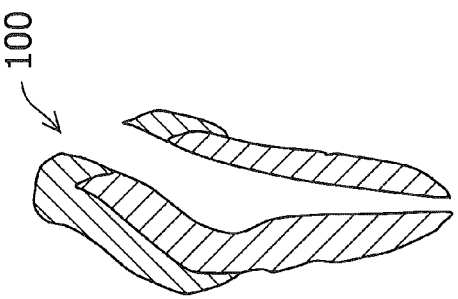
Figure 6C:
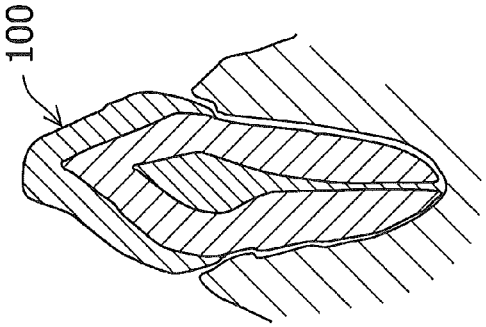
Figure 6D:
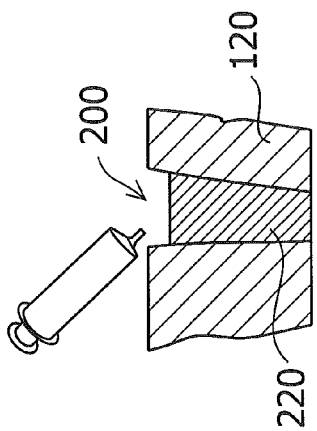
Figure 6E:
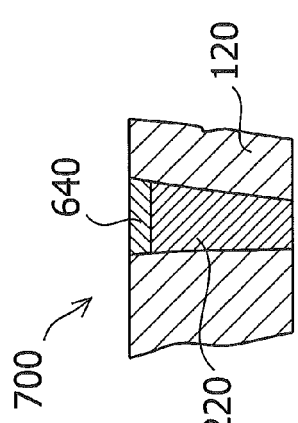
Figure 6F:
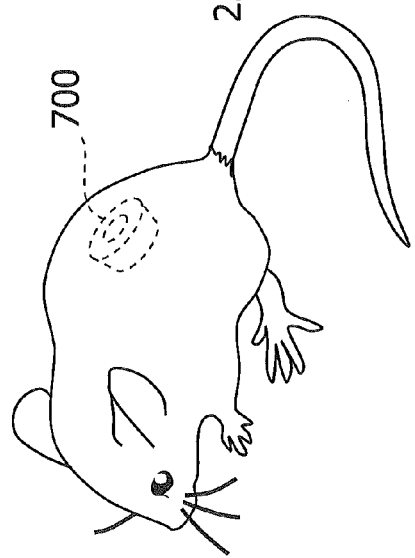
Figure 7A:
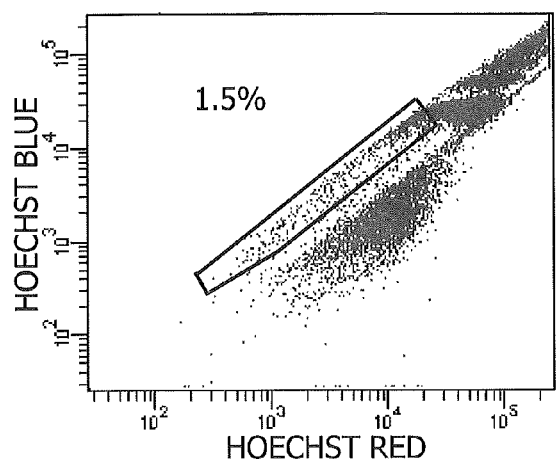
FIG. 7A shows isolation of CD31$^-$ SP cells derived from canine dental pulp tissue, wherein FIG. 7A(a) shows the results of flow cytometric analysis.
Figure 7A:
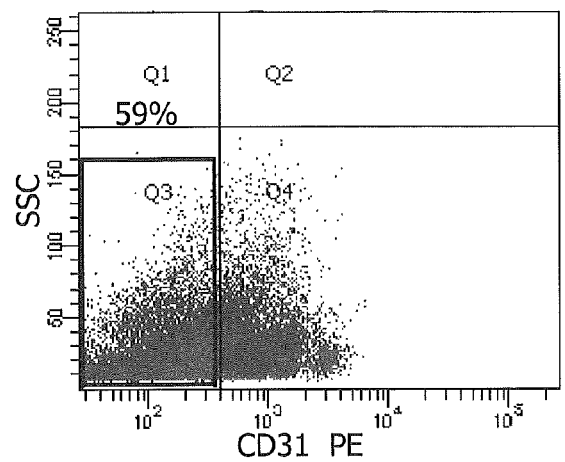
Figure 7A:
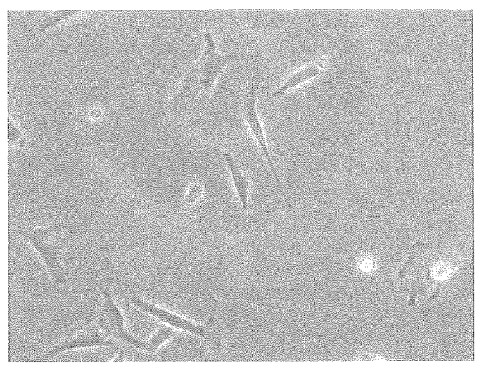
Figure 7A:
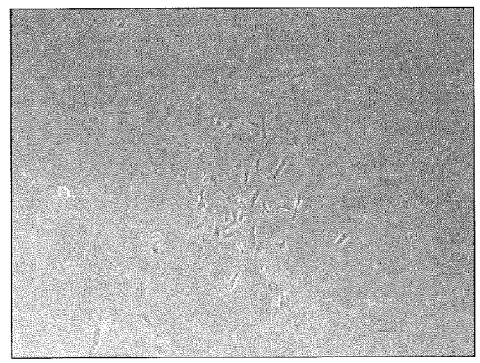
Figure 7B:
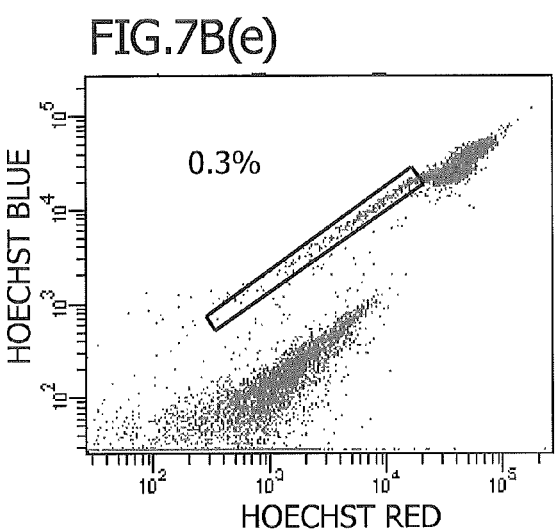
FIG. 7B shows isolation of CD31$^-$ SP cells derived from canine bone marrow tissue, wherein FIG. 7B(e) shows the results of flow cytometric analysis.
Figure 7B:
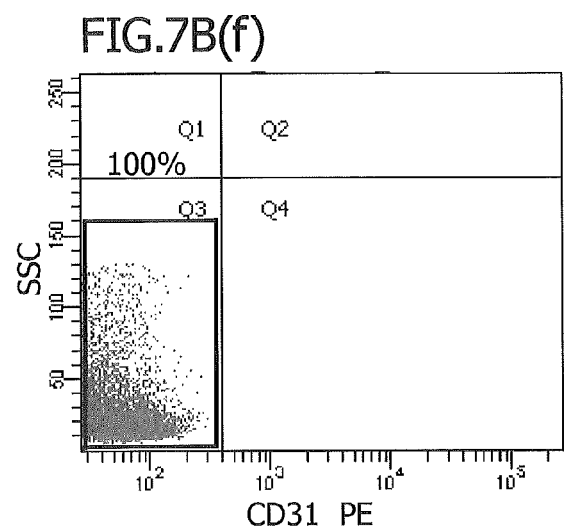
Figure 7B:
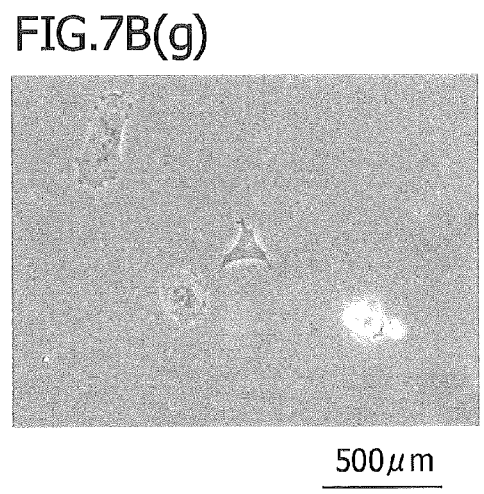
Figure 7B:
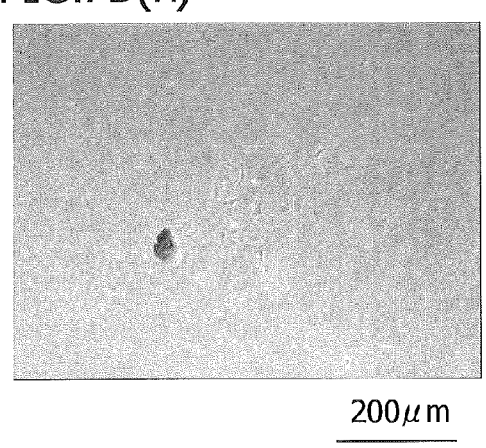

The method according to the fourth embodiment will be described with reference to FIG. 6. FIG. 6(a) shows a tooth 100 of a first individual. The tooth of the first individual used in this embodiment can be prepared by extracting the tooth from the first individual. In the step of extirpating the pulp of the tooth of the first individual, as described in the first embodiment, pulp extirpation is performed. FIG. 6(b) shows the extracted tooth 100 from which the dental pulp was removed. In the step of cutting out a predetermined length of the root portion of the tooth, the root portion of the tooth is cut out according to the size of the tissue to be regenerated. For example, the length may range from 1 to 30 mm, but this is not limited thereto. FIG. 6(c) schematically shows the root portion 120 to be cut out. In the step of sealing one end of the root canal subjected to pulp extirpation, one end of the root canal of the cut out root portion 120 is sealed with cement, for example. In the step of injecting the root canal filling material into the root canal, a filling material prepared in accordance with the method described in the first to third embodiments is injected. FIG. 6(d) shows a state of the root canal of the root portion 120 into which the root canal filling material 200 has been injected. The mesenchymal stem cells 220 of the root canal filling material 200 are attached to the apical side of the root canal. FIG. 6(e) shows the root portion 700 injected with the root canal filling material. In the step of transplanting the root injected with the root canal filling material 200 into a second individual, as shown in FIG. 6(f), the root portion 700 injected with the root canal filling material 200 is preferably transplanted under the skin of the second individual.

Subsequently, the second individual is bred for a predetermined period of time, and then the root portion 700 filled with the root canal filling material is taken out to obtain the regenerated dental tissue. The regenerated dental tissue can be further retransplanted into the alveolar bone of the first individual. The method according to the fourth embodiment can be very advantageous in that the dental tissue of one individual can be regenerated in another individual.

The present invention will now be more specifically described by examples, but is not limited to the following examples at all.

EXAMPLE 1

Regeneration of Dental Pulp by Stem Cell Derived from Canine

Cell isolation

Canine dental pulp stem cells were isolated from canine dental pulp tissue extracted from a canine upper tooth in accordance with the method described in Iohara et al., 2006 (STEM CELLS, Volume 24, Issue 11, pages 2493-2503, November 2006). Primary adipose cells and primary bone marrow cells were respectively isolated from abdominal subcutaneous fat and rib bone marrow of the identical dog. These cells were labeled with Hoechst 33342 (Sigma, St. Louis, Mo., http://www.sigmaaldrich.com) as described in Iohara et al., 2006. Subsequently, the cells were preincubated with mouse BD Fc Block (BD Biosciences, San Jose, Calif., http://www.bdbioscience.com) at 4° C. for 30 minutes to remove non-specific binding. The cells were further incubated with mouse anti-pig CD31 (PE) (LCI-4) (AbD Serotec) (Invitrogen Corporation, Carlsbad, Calif., http://www.invitrogen.com) at 4° C. for 60 minutes in PBS containing mouse IgG1 negative control (MCA928) (AbD Serotec Ltd, Oxford, UK, http://www.serotec.com), mouse IgG1 negative control (Phycoerythrin, PE) (MCA928PE) (AbD Serotec), and 20% fetal bovine serum. Subsequently, these cells were resuspended in HEPES buffer containing 2 μg/mL of propidium iodide (PI) (Sigma). The cells were analyzed and sorted using a flow cytometer (FACS-ARIA II: BD biosciences).

The CD31⁻ SP cells derived from canine dental pulp, bone marrow, and adipose cells were each seeded in a Dulbecco's modified Eagle's medium (DMEM) (Sigma) containing 10% fetal bovine serum (Invitrogen Corporation, Carlsbad, Calif., USA) in a 35-mm plate (Asahi Technoglass Corp., Funabashi, Japan, http://www.atgc.co.jp) coated with type I collagen, and the cells were cultured. The medium was replaced with fresh medium every 4 or 5 days. The cells reached 50 to 60% confluent were isolated by incubating with 0.02% EDTA at 37° C. for 10 minutes, were diluted to 1:4, and were subcultured.

Expression of Cell Surface Marker

The phenotypes of the CD31⁻ SP cells derived from canine dental pulp, bone marrow, and adipose tissue were evaluated using the cells of the third passage. The cells were immuno labeled with the following materials: mouse IgG1 negative control (AbD Serotec Ltd.), mouse IgG1 negative control (fluorescein isothiocyanate, FITC) (MCA928F) (AbD Serotec), mouse IgG1 negative control (Phycoerythrin-Cy5, PE-Cy5) (MCA928C) (AbD Serotec), mouse IgG1 negative control (Alexa 647) (MRC OX-34) (AbD Serotec), and antibodies against CD24 (Alexa Fluor 647) (ML5) (BioLegend), CD29 (PE-Cy5) (MEM-101A) (eBioscience), CD31 (FITC) (Qbend10) (Dako), CD33 (FITC) (HIM3-4) (BD Bioscience), CD34 (Allophycocyanin, APC) (1H6) (R&D Systems, Inc., Minneapolis, Minn., USA), CD44 (Phycoerythrin-Cy7, PE-Cy7) (IM7) (eBioscience), CD73 (APC) (AD2) (BioLegend), CD90 (FITC) (YKIX337.217) (AbD Serotec), CD146 (FITC) (sc-18837) (Santa Cruz Biotechnology, Santa Cruz, Calif., USA), CD150 (FITC) (A12) (AbD Serotec), MHC class I (R-PE) (3F10) (Ancell Corporation, Bayport, Minn., USA), MHC class II (APC) (TDR31.1) (Ancell), and CXCR4 (FITC) (12G5) (R&D).

Real-Time RT-PCR Analysis

In order to further evaluate the phenotype of the cell populations, total RNAs were extracted from dental pulp and adipose CD105+ cells of the third passage and total dental pulp cells using Trizol (Invitrogen). The number of cells was normalized to $5 \times 10^4$ in each experiment. First-strand cDNA was synthesized from total RNA by reverse transcription with ReverTra Ace-α (Toyobo, Tokyo, Japan). The real-time RT-PCR amplification was performed using stem cell markers: canine CXCR4, Sox2, Stat3, Bmi1, Tert, and Oct4, labeled with LightCycler Fast Start DNA master SYBR Green I (Roche Diagnostics, Pleasanton, Calif.) using LightCycler (Roche Diagnostics) at 95° C. for 10 seconds, 62° C. for 15 seconds, and 72° C. for 8 seconds. The primers used are shown below.

TABLE 1

| Gene | | 5' ← DNA Sequence → 3' | | product size | Accession number |
|---|---|---|---|---|---|
| Sox 2 | Forward | AGCTAGTCTCCAAGCGACGA | (SEQ ID NO: 1) | 193 bp | XM_545216 |
| | Reverse | CCACGTTTGCAACTGTCCTA | (SEQ ID NO: 2) | | |
| Bmi1 | Forward | CACTCCCGTTCAGTCTCCTC | (SEQ ID NO: 3) | 150 np | XM_544225 |
| | Reverse | CCAGATGAAGTTGCTGACGA | (SEQ ID NO: 4) | | |
| CXCR4 | Forward | CTGTGGCAAACTGGTACTTC | (SEQ ID NO: 5) | 210 bp | NM_001048026 |
| | Reverse | TCAACAGGAGGGCAGGTATC | (SEQ ID NO: 6) | | |
| Stat3 | Forward | GTGGTGACGGAGAAGCAACA | (SEQ ID NO: 7) | 191 bp | XM_844672 |
| | Reverse | TTCTGTCTGGTCACCGACTG | (SEQ ID NO: 8) | | |
| GM-CSF | Forward | GCAGAACCTGCTTTTCTTGG | (SEQ ID NO: 9) | 195 bp | S49738 |
| | Reverse | CCCTCAGGGTCAAACACTTC | (SEQ ID NO: 10) | | |
| MMP3 | Forward | CCCTCTGATTCCTCCAATGA | (SEQ ID NO: 11) | 210 bp | AY183143 |
| | Reverse | GGATGGCCAAAATGAAGAGA | (SEQ ID NO: 12) | | |
| VEGFA | Forward | CTACCTCCACCATGCCAAGT | (SEQ ID NO: 13) | 183 bp | NM_001003175 |
| | Reverse | ACGCAGGATGGCTTGAAGAT | (SEQ ID NO: 14) | | |
| BDNF | Forward | GTTGGCCGACACTTTTGAAC | (SEQ ID NO: 15) | 202 bp | NM_001002975 |
| | Reverse | CCTCATCGACATGTTTGCAG | (SEQ ID NO: 16) | | |
| GDNF | Forward | GCCGAGCAGTGACTCAAAC | (SEQ ID NO: 17) | 104 bp | XM_546342 |
| | Reverse | TCTCGGGTGACCTTTTCAG | (SEQ ID NO: 18) | | |

TABLE 1-continued

| Gene | | 5' ← DNA Sequence → 3' | product size | Accession number |
|---|---|---|---|---|
| NGF | Forward | CAACAGGACTCACAGGAGCA (SEQ ID NO: 19) | 156 bp | XM_540250 |
| | Reverse | ATGTTCACCTCTCCCAGCAC (SEQ ID NO: 20) | | |
| β-actin | Forward | AAGTACCCCATTGAGCACGG (SEQ ID NO: 21) | 257 bp | Z70044 |
| | Reverse | ATCACGATGCCAGTGGTGCG (SEQ ID NO: 22) | | |

TABLE 2

| Gene | | 5' ← DNA Sequence → 3' | product size | Accession number |
|---|---|---|---|---|
| Syndecan 3 | Forward | TCATGCAGGACAGCTTCAAC (SEQ ID NO: 23) | 186 bp | XM_544449 |
| | Reverse | AGGGCTGGAATCTAGGGAAA (SEQ ID NO: 24) | | |
| Tenascin-C | Forward | TGGCTGTCTTGGACACAGAG (SEQ ID NO: 25) | 181 bp | XM_538811 |
| | Reverse | GACTCCAGAGTTGGGGTCTG (SEQ ID NO: 26) | | |
| Vimentin | Forward | GGAGCAGCAGAACAAGATCC (SEQ ID NO: 27) | 230 bp | XM_847574 |
| | Reverse | TCTCGGCTTCCTCTCTCTGA (SEQ ID NO: 28) | | |
| ALPase | Forward | CCATCCTGTATGGCAATGG (SEQ ID NO: 29) | 65 bp | AF540075 |
| | Reverse | TGAACGAGAGAATGTCTCCATG (SEQ ID NO: 30) | | |
| Periostin | Forward | AAACCATTGGAGGCAAACAG (SEQ ID NO: 31) | 209 bp | XM_534490 |
| | Reverse | TGCAGCTTCAAGTAGGCTGA (SEQ ID NO: 32) | | |
| PLAP-1 | Forward | TCCCGTCAGGATTACAGGAG (SEQ ID NO: 33) | 210 bp | XM_848228 |
| | Reverse | GAACGCTCATTCTGCTCACA (SEQ ID NO: 34) | | |
| ap2 | Forward | CGGATGACAGAAAAGTCAAG (SEQ ID NO: 35) | 194 bp | XM_543759 |
| | Reverse | TTCAGCTTGATGTCCCTTGG (SEQ ID NO: 36) | | |
| DSPP | Forward | GTCCTAGTGGGAATGGAGCA (SEQ ID NO: 37) | 190 bp | XM_544971 |
| | Reverse | TCTTCAGGGCCATCATCTTC (SEQ ID NO: 38) | | |

In order to investigate the expression of angiogenic factor and neurotrophic factor mRNAs, the real-time RT-PCR amplification of canine matrix metalloprotease-3 (MMP-3), VEGF-A, granulocyte/monocyte colony-stimulating factor (GM-CSF), SDF-1, NGF, BDNF, neuropeptide Y, and neurotrophin 3 was also performed (Iohara et al., submitted). The expressions of bone marrow and adipose CD31$^-$ SP cells were normalized with beta-actin and were then compared with that of dental pulp CD31$^-$ SP cells.

Induction of Differentiation

Differentiation of canine bone marrow and adipose CD31$^-$ SP cells of the third to fifth passages to angiogenic cells and neuronal cells was compared with differentiation of dental pulp CD31$^-$ SP cells described in Iohara et al., 2006. Regarding the neuronal differentiation, expression of neurofilament, neuromodulin, and sodium channel, voltage-gated, type Iα (Scn1α) was investigated.

Growth and Migration Assay

In order to determine cell growth responding to stromal cell-derived factor 1 (SDF1) (Acris, Herford, Germany), canine bone marrow and adipose CD31$^-$ SP cells were compared with dental pulp CD31$^-$ SP cells of the fourth passage under conditions of $10^3$ cells per well of a 96-well plate in a Dulbecco's modified Eagle's medium (DMEM) containing 0.2% fetal bovine albumin (Sigma) and SDF-1 (50 ng/mL) 10 μL of Tetra-color one (registered trademark) (Seikagaku Kogyo, Co., Tokyo, JAPAN) was added to each well of the 96-well plate, and absorbance at a wavelength of 450 nm was measured with a spectrophotometer at 2, 12, 24, and 36 hours after starting of culturing to determine the number of cells. A well not containing the cells was used as negative control.

In order to investigate the migration activity of bone marrow and adipose CD31$^-$ SP cells compared with that of dental pulp CD31$^-$ SP cell, horizontal chemotaxis assay of SDF-1 was performed. Real-time horizontal chemotaxis of cells was detected with TAXI Scan-FL (Effector Cell Institute, Tokyo, JAPAN). TAXI Scan-FL is composed of an etched silicon substrate and a flat glass plate forming two compartments having a microchannel with a depth of 6 μm. Each cell fraction ($10^5$ cells/mL: 1 μL) was injected into one hole connecting to a device equipped with a stainless steel holder, and 1 μL of 10 ng/μL of SDF-1 was injected into the hole on the opposite side. The video images of cell migration were taken for 6 hours.

In Vivo Transplantation

Experimental models of removal of dental pulp and transplantation of cell populations were established with canine permanent teeth (Narc, Chiba, Japan) with completely formed roots and closed root canals. The entire dental pulp was removed from the second incisor teeth in the upper jaw and the third incisor teeth in the lower jaw on both sides after injecting pentobarbital sodium (Schering-Plough, Germany) into veins, and then the root canal of the apex portion of each tooth was enlarged to a diameter of 0.7 mm or more with #70K-file (MANI, INC, Tochigi, Japan). Root canal filling materials composed of a first composition including 10 μL of collagen TE (Nitta Gelatin Inc.) and $5 \times 10^5$ canine dental pulp, bone marrow, or adipose CD31$^-$ SP cells of the third or fourth passage labeled with DiI and a second composition including 10 μL of collagen TE and SDF-1 at a final concentration of 15 ng/μL were prepared. The root canals were filled with the filling materials in such a manner that the first composition was autologously transplanted into the lower root canal and the second composition was placed at the upper root canal. After filling, the hole at the upper portion was sealed with zinc phosphate cement (Elite Cement, GC, Tokyo, Japan) and complex resin (Clearfil Mega Bond, Kuraray) and was then treated with an adhesive (Clearfil MegaBond, Kuraray). Sixty teeth from 15 canines were used. Dental pulp, bone marrow, and adipose CD31⁻ SP cells were respectively transplanted into 10 teeth together with SDF-1, and the teeth were extracted 14 days and 28 days later.

In order to perform morphological analysis, the teeth were fixed with 4% paraformaldehyde PFA) (Nacarai Tesque, Kyoto, Japan) at 4° C. overnight, desalted with 10% formic acid, and embedded in paraffin wax (Sigma). Each paraffin section (thickness: 5 μm) was stained with hematoxylin/eosin (HE) and was subjected to morphological analysis. In staining of blood vessels, the paraffin section with a thickness of 5 μm was deparaffinized and was stained with Fluorescein Griffonia (*Bandeiraea*) *Simplicifolia* Lectin 1/fluorescein-*galanthus nivalis* (snowdrop) lectin (20 μg/mL, Vector laboratories, Inc., Youngstown, Ohio) for 15 minutes for monitoring the presence and localization of the transplanted cells in relation to newly formed blood vessels. In the monitoring, a fluorescence microscope BIOREVO, BZ-9000 (KEYENCE, Osaka, Japan) was used.

Subsequently, in staining of nerves, the paraffin section with a thickness of 5 μm was deparaffinized and was incubated together with 0.3% Triton X-100 (Sigma Chemical; St Louis, Mo.) for 15 minutes. After incubation with 2.0% normal goat serum for blocking of non-specific binding, the section was incubated together with goat anti-human PGP 9.5 (Ultra Clone Ltd.) (1:10000) at 4° C. overnight. After washing with PBS three times, the bound antibody was reacted with a biotinylated goat anti-rabbit IgG secondary antibody (Vector) (1:200) at room temperature for 1 hour. The section was also developed using DAB chromogen together with an ABC reagent (Vector Laboratories, Burlingame, Calif.) for 10 minutes.

The relative amount of regenerated dental pulp in each sample on the 14th day after the transplantation was determined from the image of the whole tooth taken with a stereoscopic microscope (Leica, M205FA). Five teeth transplanted with canine dental pulp, bone marrow, or adipose CD31⁻ SP cells and SDF-1 were each investigated for three sections prepared with an interval of 150 μm. The outlines of pictures of newly regenerated dental pulp tissue and dentin on a screen were traced, and the surface areas defined by the outlines of the root canal were determined using Leica Application Suite software. The ratio of the regenerated area to the root canal area was calculated for three sections of each tooth, and the average value was determined. The statistical analysis was performed by an unpaired Student's t-test. The data are each shown as mean±standard deviation of measurements taken five times.

In order to compare regenerated tissue in transplantation of three different cells, regarding periodontal ligament, the real-time RT-PCR amplification was also performed using the above-mentioned markers: canine axin 2, periostin, asporin/periodontal ligament-associated protein 1 (PLAP-1), syndecan 3, tenascin C, TRH-DE, vimentin, and alkaline phosphatase.

Statistical Analysis

The data shown as mean±standard deviation were calculated using an unpaired Student's t test. Each experiment was repeated three times, and one representative experiment was presented in the drawings and tables.

Results

Isolation and evaluation of CD31⁻ SP cells derived from canine dental pulp, bone marrow, and adipose tissue The results of flow cytometry analysis demonstrate that SP cells derived from canine dental pulp, bone marrow, and adipose tissue from the same individual were present in amounts of 1.5%, 0.3%, and 0.1%, respectively, relative to the total cells (FIGS. 7(*a*), (*e*), and (*i*)). In addition, it was revealed that CD31⁻ SP cells derived from canine dental pulp, bone marrow, and adipose tissue were present in amounts of 0.9%, 0.3%, and 0.1%, respectively, relative to the total cells (FIGS. 7(*b*), (*f*), and (*j*)). These three CD31⁻ SP cell populations showed similar cell phenotypes, i.e., they included stellate cells with a few long processes and spindle cells. The stellate cells had a large nucleus surrounded by granules. The spindle cells were neuron-like cells having long and thin processes and a small amount of cytoplasm. These are shown in FIGS. 7(*c*), (*d*), (*g*), (*h*), (*k*), and (*l*). A single canine dental pulp CD31⁻ SP cell and a single adipose CD31⁻ SP cell seeded in a 35-mm plate each formed a colony in 10 days, and a single canine bone marrow CD31⁻ SP cell formed a colony in 14 days. The results demonstrate that these cells have colony-forming activities. The efficiencies of attachment and growth of canine dental pulp, bone marrow, and adipose CD31⁻ SP cells were estimated to be 8%, 6%, and 7%, respectively. Limiting dilution analysis at the third passage culture showed that the frequency of dental pulp CFU of canine dental pulp CD31⁻ SP cells, canine bone marrow CD31⁻ SP cells, and canine adipose CD31⁻ SP cells was estimated to be 80%, 75%, and 80%, respectively.

"Traits as a stem cell (Stemness)" of a canine dental pulp CD31⁻ SP cell were compared with those of canine bone marrow and adipose CD31⁻ SP cells by flow cytometry analysis of cell surface antibody markers. These three CD31⁻ SP cell populations were positive for CD29, CD44, and CD90. The proportion of CD34+ cells in canine dental pulp CD31⁻ SP cells was 4.4%, which proportion was lower compared with 9.8% and 7.1% in canine bone marrow CD31⁻ SP cells and canine adipose CD31⁻ SP cells, respectively. The proportions of CD 105+ cells in canine dental pulp CD31⁻ SP cells and canine bone marrow CD31⁻ SP cells were 60.2% and 64.9%, respectively, which proportions were low compared with 85.5% in canine adipose CD31⁻ SP cells. The fourth passages of these populations were substantially negative for CD146. The expression levels of CXCR4 in canine dental pulp and adipose CD31⁻ SP cells were higher than that in canine bone marrow CD31⁻ SP cells. The results are shown in Table 3.

TABLE 3

|  | Pulp CD31⁻SP | Bone marrow CD31⁻SP | Adipose CD31⁻SP |
| --- | --- | --- | --- |
| CD29 | 85.7 | 88.9 | 86.2 |
| CD34 | 4.4 | 9.8 | 7.1 |
| CD44 | 99.4 | 99.7 | 99.8 |
| CD73 | 84.7 | 86.4 | 85.4 |
| CD90 | 90.2 | 89.3 | 89.1 |
| CD105 | 60.2 | 64.9 | 85.5 |
| CD146 | 0.7 | 0.3 | 0.6 |
| CD150 | 1.8 | 1.3 | 1.8 |
| CD271 | 2.7 | 1.4 | 1.8 |
| CXCR4 | 2.7 | 0.5 | 2.7 |

Expression levels of stem cell markers, Stat3, Bmi1, Sox2, Tert, and CXCR4, in canine dental pulp CD31⁻ SP cells were comparable to those in canine bone marrow and adipose CD31⁻ SP cells. The results suggest that these three cell populations have similar properties as stem cells. The expression levels of the angiogenic and/or neurotrophic factors, NGF, VEGF-A, and MMP-3, in canine dental pulp CD31⁻ SP cells were higher than those in canine bone marrow and adipose CD31⁻ SP cells. The expression level of BDNF in canine bone marrow CD31⁻ SP cells was higher than those in canine dental pulp and adipose CD31⁻ SP cells. GDNF was similarly expressed in all three cell populations. The results are shown in Table 4.

TABLE 4

|  | BM/pulp | adipose/pulp |
|---|---|---|
| Sox 2 | 5.9 | 0.9 |
| Tert | 1.2 | 1.0 |
| Bmi 1 | 0.9 | 1.2 |
| CXCR4 | 0.9 | 1.7 |
| Stat 3 | 1.1 | 0.6 |
| GM-CSF | 0.6 | 0.2 |
| MMP 3 | 0.2 | 0.2 |
| VEGF | 0.4 | 0.5 |
| BDNF | 5.1 | 2.1 |
| GDNF3 | 1.2 | 1.0 |
| NGF | 0.7 | 0.8 |

The differentiation potentials of CD31⁻ SP cells into vascular endothelial cells (FIGS. 8(a), (b), and (c)), neurospheres (FIGS. 8(d), (e), and (f)), and neuronal cells (FIGS. 8(g), (h), and (i)) were compared among the three cell populations, canine dental pulp, bone marrow, and adipose CD31⁻ SP cells. Extensive networks of cords and tube-like structures were observed on matrigel as early as 12 hours cultivation in all cell populations (FIGS. 8(a), (b), and (c)). Clusters and proliferating neurospheres were detected 14 days after induction. The three cell populations showed little difference in incidence and amount of neurospheres. In addition, neuronal induction from these neurospheres was successfully performed. Most of the cells in these three cell populations were immunoreactive with neuromodulin. Neuronal markers, neurofilament, neuromodulin, and Scn1α mRNA, were expressed in all of the three cell populations (FIG. 8(j)).

Migration and Growth

Figure 9A:
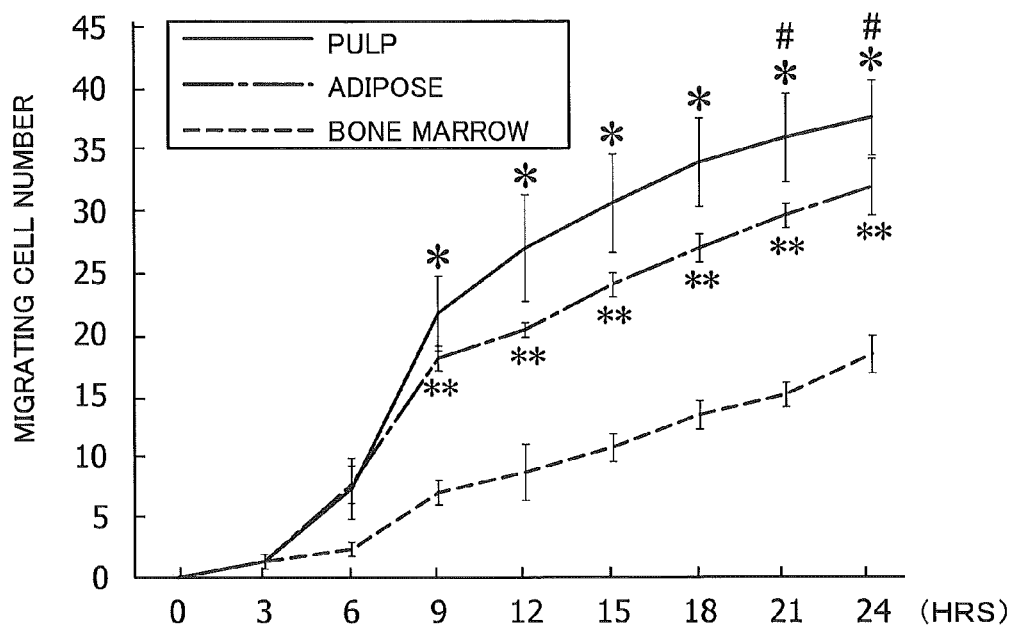
FIG. 9 shows migration and growth effects by stromal cell-derived factor 1 on canine dental pulp, bone marrow, and adipose CD31$^-$ SP. Data are expressed as means±standard deviation of four determinations. The experiment was repeated three times, and one representative experiment is presented. The graph (a) shows the migration activity on 0, 3, 6, 9, 12, 15, 18, 21, and 24 hours after culturing using SDF-1 (10 ng/mL). *: P<0.001, dental pulp vs. bone marrow; #: P<0.05, dental pulp vs. adipose, **: P<0.001, bone marrow vs. adipose. The graph (b) shows the growth activity on 2, 18, 26, and 44 hours after culturing using SDF-1 (10 ng/mL).
Figure 9B:
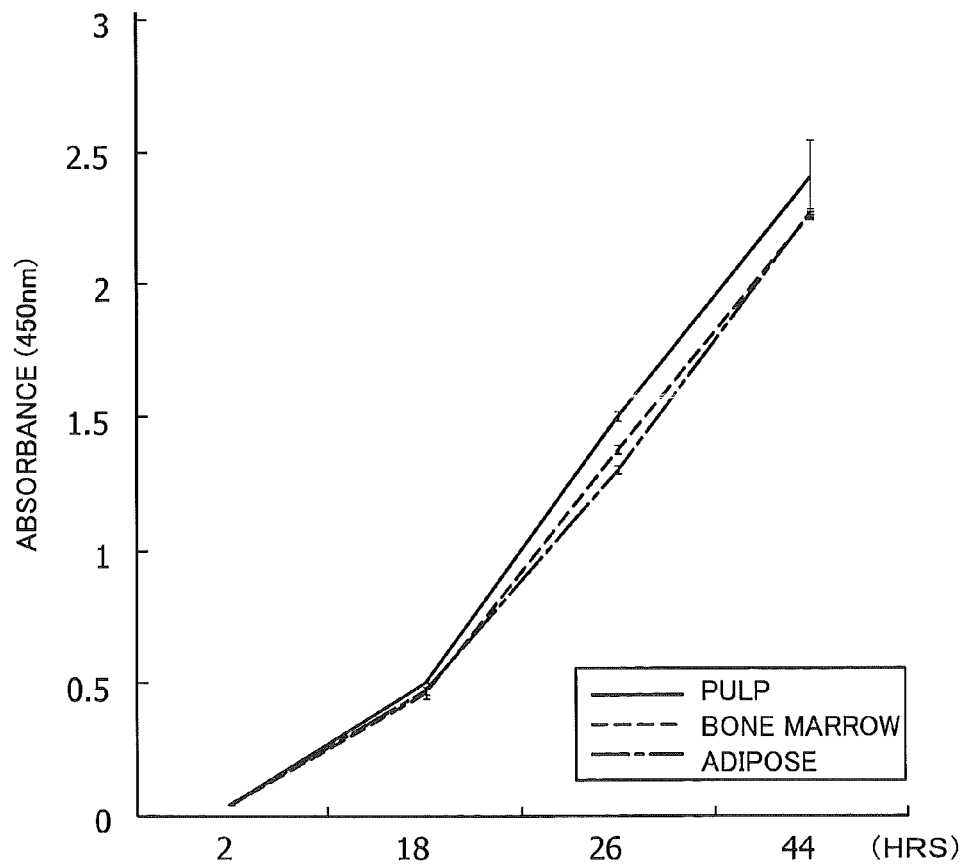
Figure 10B:
FIG. 10B shows complete regeneration of dental pulp tissue in autologous transplantation of a filling material according to the present invention into a canine root canal after pulp extirpation, wherein (k), (n), and (q) are microscopic images when canine dental pulp CD31$^-$ SP was transplanted; (l), (o), and (r) are those when canine bone marrow CD31$^-$ SP was transplanted; and (m), (p), and (s) are those when canine adipose CD31$^-$ SP was transplanted, wherein (k), (l), and (m) are confocal microscopic images showing the results of BS-1 lectin immunostaining showing newly formed capillary vessels; (n), (o), and (p) show the results of PGP 9.5 immunostaining; and (q), (r), and (s) show the results of Masson's trichrome staining showing matrix formation.
Figure 10B:
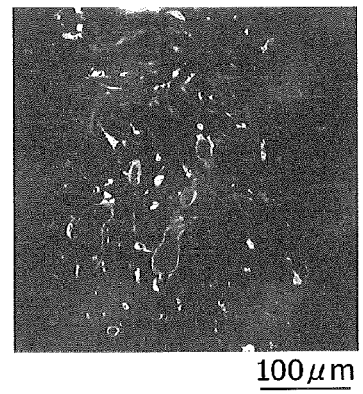
Figure 10B:
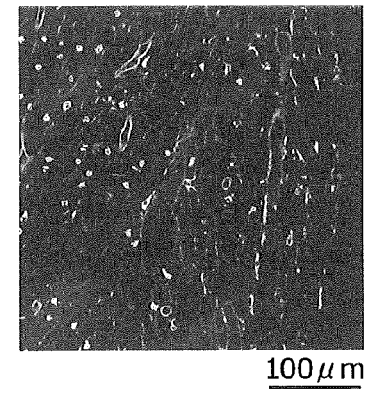
Figure 10B:
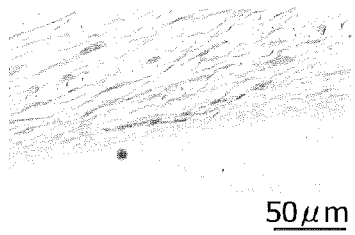
Figure 10B:
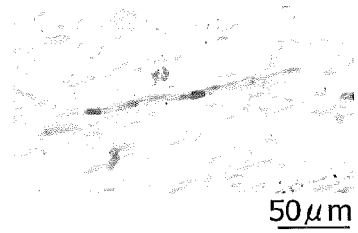
Figure 10B:
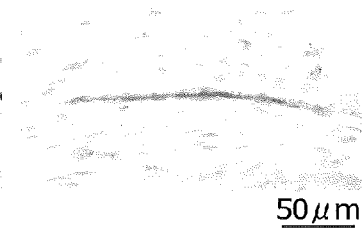
Figure 10B:
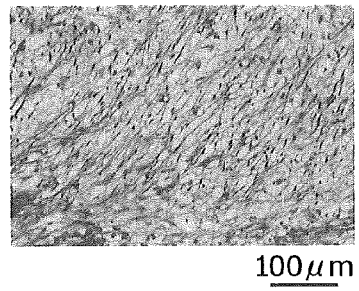
Figure 10B:
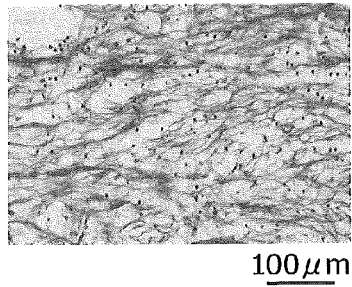
Figure 10B:
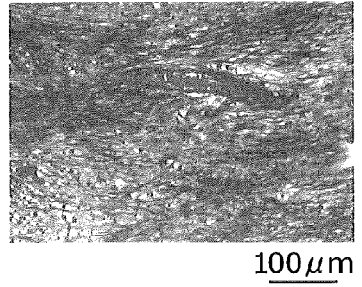

The migration activity, which is indicated by TAXI Scan-FL, when SDF-1 existed together was relatively high in canine dental pulp CD31⁻ SP cells and adipose CD31⁻ SP cells and was lower in canine bone marrow CD31⁻ SP cells compared with the other two (FIG. 9(a)). The proliferation activity with SDF-1 was the same in all canine dental pulp, bone marrow and adipose CD31⁻ SP cells (FIG. 9(b)).

Regeneration of Dental Pulp after Transplantation into Root Canal

Subsequently, in vivo autologous transplantation of canine dental pulp, bone marrow, or adipose CD31⁻ SP cells together with SDF-1 into the root canal of a canine permanent tooth with complete root formation and a closed root canal subjected to pulp extirpation was evaluated (FIG. 10). In transplantation of the dental pulp and adipose CD31⁻ SP cells together with SDF-1, formation of dental pulp-like tissue was detected on the 14th day after transplantation (FIG. 10(a) and (c)). However, in transplantation of the bone marrow CD31⁻ SP cells together with SDF-1, the amount of regenerated dental pulp was smaller than that in transplantation of dental pulp and adipose CD31⁻ SP cells together with SDF-1 (FIG. 10(b)). The results of statistical analysis demonstrate that the regenerated areas in transplantation of dental pulp CD31⁻ SP cells and adipose CD31⁻ SP cells together with SDF-1 were larger (2.0 times and 1.5 times increase, respectively), compared with that in transplantation of bone marrow CD31⁻ SP cells together with SDF-1 and that those were thus statistically significant (FIG. 10(j)). In all transplantations of the three types of cells, the cells in the regenerated tissue were stellate or spindle (FIGS. 10(d), (e), and (f)). However, fibrous matrix formation was partially observed in transplantations of bone marrow and adipose CD31⁻ SP cells (FIGS. 10(e) and (f)). Furthermore, strong calcification was observed in dental pulp on the 90th day after transplantation of adipose CD31⁻ SP cells together with SDF-1 (FIG. 10(i)), whereas calcification was hardly observed in transplantation of dental pulp CD31⁻ SP cells together with SDF-1 and was slightly observed in transplantation of bone marrow CD31⁻ SP cells together with SDF-1. Confocal laser microscopic analysis of frozen sections stained with BS-1 lectin revealed that angiogenesis occurred in the regenerated tissue (FIGS. 10(k), (l), and (m)). Neurites stained with an antibody extended into the dental pulp newly regenerated from the apical foramen (FIGS. 10(n), (o), and (p)). The results of Masson's staining showed strong matrix formation on the 90th day after transplantation of adipose CD31⁻ SP cells together with SDF-1.

The expression levels of periostin mRNAs in tissue regenerated by transplantation of canine dental pulp, bone marrow, and adipose CD31⁻ SP cells were considerably less than that in normal periodontal ligament tissue. It was revealed that syndecan 3, tenascin C, and vimentin, which are known to be highly expressed in dental pulp, were expressed in all regenerated tissue as in those in normal dental pulp tissue. All of differentiation markers of adipose, bone, dentin, aP2, Osterix, and Dspp were not expressed in all regenerated tissue. The results are shown in Table 5.

TABLE 5

|  | Regenerated tissue (pulp CD31-SP) | Regenerated tissue (bone marrow CD31-SP) | Regenerated tissue (adipose CD31-SP) | normal pulp | normal periodontal tissue | Adipose cells |
|---|---|---|---|---|---|---|
| syndecan | 0.4 | 0.5 | 0.5 | 1.0 | 0 | 0 |
| Tenascin | 0.2 | 0.2 | 0.4 | 1.0 | 0.1 | 0 |
| vimentin | 0.2 | 0.5 | 0.6 | 1.0 | 0.6 | 0 |
| ALPase | 0.5 | 0.5 | 0.3 | 1.0 | 1.5 | 0 |
| periostin | 0 | 0 | 0.1 | 0 | 1.0 | 0 |
| PLAP | 0.1 | 0.2 | 0.5 | 0 | 1.0 | 0.2 |
| aP2 | 0 | 0 | 0 | 0 | 4.0 | 1.0 |
| Dspp | 0 | 0 | 0 | 0 | 0 | 0 |

EXAMPLE 2

Regeneration of Dental Pulp by Stem Cell Derived from Pig

Cell Isolation

Primary dental pulp cells were isolated from a pig tooth germ. Pig primary adipose cells and primary bone marrow cells were both isolated from the lower jaw of the same pig. These cells were labeled with Hoechst 33342 (Sigma, St. Louis, Mo., http://www.sigmaaldrich.com) in accordance with the method described in Iohara et al., 2006. Subsequently, the cells were preincubated with mouse BD Fc Block (BD Biosciences, San Jose, Calif., http://www.bdbioscience.com) at 4° C. for 30 minutes to remove non-specific binding. The cells were further incubated with mouse anti-pig CD31 (PE) (LCI-4) (AbD Serotec) (Invitrogen Corporation, Carlsbad, Calif., http://www.invitrogen.com) at 4° C. for 60 minutes in PBS containing mouse IgG1 negative control (MCA928) (AbD Serotec Ltd, Oxford, UK, http://www.serotec.com), mouse IgG1 negative control (Phycoerythrin, PE) (MCA928PE) (AbD Serotec), and 20% fetal bovine serum. Subsequently, these cells were resuspended in HEPES buffer containing 2 μg/mL of propidium iodide (PI) (Sigma). The cells were analyzed and sorted using a flow cytometer (FACS-ARIA II: BD biosciences).

The CD31⁻ SP cells derived from pig dental pulp, bone marrow, and adipose cells were each seeded in EBM2 containing 10% fetal bovine serum (Invitrogen Corporation, Carlsbad, Calif., USA) and 5 ng/mL of EGF (Cambrex Bio Science) in a 35-mm plate (Asahi Technoglass Corp., Funabashi, Japan, http://www.atgc.co.jp) coated with type I collagen, and the cells were cultured. The medium was replaced with new medium every 4 or 5 days. The cells reached 50 to 60% confluent were isolated by incubating with 0.02% EDTA at 37° C. for 10 minutes, were diluted to 1:4, and were subcultured.

Expression of Cell Surface Marker

The phenotypes of the CD31⁻ SP cells derived from pig dental pulp, bone marrow, and adipose tissue were evaluated using the cells of the third passage. The cells were analyzed by flow cytometry through immunolabeling with the following antibodies: mouse IgG1 negative control (AbD Serotec Ltd.), mouse IgG1 negative control (fluorescein isothiocyanate, FITC) (MCA928F) (AbD Serotec), mouse IgG1 negative control (Phycoerythrin-Cy5, PE-Cy5) (MCA928C) (AbD Serotec), mouse IgG1 negative control (Alexa 647) (MRC OX-34) (AbD Serotec), and antibodies against CD14 (Alexa Fluor 647) (Tuk4) (AbD Serotec), CD29 (PE-Cy5) (MEM-101A) (eBioscience), CD31 (PE) (LCI-4) (AbD Serotec), CD34 (PE) (581) (Beckman Coulter), CD44 (PE-Cy5) (IM7) (eBioscience), CD73 (Alexa Flour 647) (AD2) (eBioscience), CD90 (Alexa Flour 647) (F15-42-1) (AbD Serotec), CD105 (FITC) (MEM-229) (Abcam), CD117/c-kit (Allophycocyanin, APC) (A3C6E2) (Miltenyi Biotec, Bergisch Gladbach, Germany, http://www.miltenyibiotec.com), CD133 (Alexa Flour 647) (293C3) (Miltenyi Biotec), CD146 (FITC) (OJ79c) (AbD Serotec), CD150 (FITC) (A12) (AbD Serotec), CD271 (APC) (ME20.4-1H4) (Miltenyi Biotec.), and CXCR4 (FITC) (12G5) (R&D).

Real-Time RT-PCR Analysis of Stem Cell Markers, Angiogenic Factors, and Neurotrophic Factors In order to investigate stem cell characteristics, angiogenic potential, and neurogenic potential of CD31⁻ SP cell populations derived from pig dental pulp, bone marrow, and adipose tissue, total RNA was extracted from each CD31⁻ SP cell with Trizol (Invitrogen). The number of cells was normalized to 5×10⁴ in each experiment. First-strand cDNA was synthesized from total RNA by reverse transcription with ReverTra Ace-α (Toyobo, Tokyo, Japan). The real-time RT-PCR amplification was performed using stem cell markers: pig C Sox2, Tert, Bmi1, CXCR4, and Stat3, and an angiogenic factor, a neurotrophic factor, a granulocyte/monocyte colony-stimulating factor (GM-CSF), matrix metalloprotease-3 (MMP-3), vascular endothelial growth factor A (VEGF-A), a brain-derived neurotrophic factor (BDNF), a glial cell line-derived neurotrophic factor (GDNF), a nerve growth factor (NGF), neuropeptide Y (Iohara et al., 2008 (STEM CELLS, Volume 26, Issue 9, pages 2408-2418, September 2008); Sugiyama et al., 2011 (Tissue Engineering Part A. January 2011)), labeled with LightCycler Fast Start DNA master SYBR Green I (Roche Diagnostics, Pleasanton, Calif.) using LightCycler (Roche Diagnostics) at 95° C. for 10 seconds, 62° C. for 15 seconds, and 72° C. for 8 seconds. The expressions of bone marrow and adipose CD31⁻ SP cells were normalized with beta-actin and were then compared with that of dental pulp CD31⁻ SP cells. The primers used are shown below.

TABLE 6

| Gene | | 5' ← DNA Sequence → 3' | product size | Accession number |
|---|---|---|---|---|
| Sox 2 | Forward | AATGCCTTCATGGTGTGGTC (SEQ ID NO: 39) | 203 bp | DQ400923 |
| | Reverse | CGGGGCCGGTATTTATAATC (SEQ ID NO: 40) | | |
| Tert | Forward | CAGGTGTACCGCCTCCTG (SEQ ID NO: 41) | 180 bp | DQ400924 |
| | Reverse | CCAGATGCAGTCTTGCACTT (SEQ ID NO: 42) | | |
| Bmi1 | Forward | ATATTTACGGTGCCCAGCAG (SEQ ID NO: 43) | 179 bp | CK451985 |
| | Reverse | GAAGTGGCCCATTCCTTCTC (SEQ ID NO: 44) | | |
| CXCR4 | Forward | CCGTGGCAAACTGGTACTTT (SEQ ID NO: 45) | 210 bp | NM_213773 |
| | Reverse | TCAACAGGAGGGCAGGTATC (SEQ ID NO: 46) | | |
| Stat3 | Forward | GTGGTGACAGAGAAGCAGCA (SEQ ID NO: 47) | 191 bp | CK453710 |
| | Reverse | TTCTGCCTGGTCACTGACTG (SEQ ID NO: 48) | | |
| GM-CSF | Forward | TGTGGATGCCATCAAAGAAG (SEQ ID NO: 49) | 217 bp | U61139 |
| | Reverse | GTGCTGCTCATAGTGCTTGG (SEQ ID NO: 50) | | |
| MMP3 | Forward | ACCCAGATGTGGAGTTCCTG (SEQ ID NO: 51) | 171 bp | AB044413 |
| | Reverse | GGAGTCACTTCCTCCCAGATT (SEQ ID NO: 52) | | |
| VEGF-A | Forward | CTACCTCCACCATGCCAAGT (SEQ ID NO: 53) | 183 bp | NM_214084 |
| | Reverse | ACACAGGACGGCTTGAAGAT (SEQ ID NO: 54) | | |
| BDNF | Forward | TTCAAGAGGCCTGACATCGTCGT (SEQ ID NO: 55) | 180 bp | NM_214259 |
| | Reverse | AGAAGAGGAGGCTCCAAAGG (SEQ ID NO: 56) | | |
| GDNF | Forward | ACGGCCATACACCTCAATGT (SEQ ID NO: 57) | 144 bp | XM_003133897 |
| | Reverse | CCGTCTGTTTTTGGACAGGT (SEQ ID NO: 58) | | |
| NGF | Forward | TGGTGTTGGGAGAGGTGAAT (SEQ ID NO: 59) | 210 bp | L31898 |
| | Reverse | CCGTGTCGATTCGGATAAA (SEQ ID NO: 60) | | |
| β-actin | Forward | CTCTTCCAGCCCTCCTTCCT (SEQ ID NO: 61) | 80 bp | AJ312193 |
| | Reverse | ACGTCGCACTTCATGATCGA (SEQ ID NO: 62) | | |

Transplantation into Tooth Root Model

In order to examine ectopic dental pulp regeneration, subcutaneous transplantation of a pig tooth root model was performed. The third incisor teeth were extracted from pigs, and the roots thereof were each sliced to a length of 6 mm. The root canal was enlarged to a width of 1 mm and was then sealed with MTA cement at one end. Root canal filling materials composed of $1\times10^6$ pig dental pulp, bone marrow, or adipose CD31⁻ SP cell populations of the third or fourth passage and 10 μL of collagen TE (Nitta Gelatin Inc., Osaka, Japan) were prepared. The filling materials were each injected into the root having a sealed one end. The roots were subcutaneously transplanted into 5-week old SCID mice (CB17, CLEA, Tokyo, JAPAN, http://www.clea-japan.com). Dental pulp, bone marrow, and adipose CD31⁻ SP cells derived from pigs of four different individuals were each transplanted into two tooth roots. In order to perform histological study, 24 roots in total were extracted 14 days later.

In order to perform morphological analysis, the roots were fixed with 4% paraformaldehyde PFA (Nacarai Tesque, Kyoto, Japan) at 4° C. overnight, desalted with 10% formic acid, and then embedded in paraffin wax (Sigma). Each paraffin section (thickness: 5 μm) was stained with hematoxylin/eosin (HE) and was then subjected to morphological analysis. For staining of blood vessels, the paraffin section with a thickness of 5 μm was deparaffinized and was stained with Fluorescein Griffonia (*Bandeiraea*) *Simplicifolia* Lectin 1/fluorescein-*galanthus nivalis* (snowdrop) lectin (20 μg/mL, Vector laboratories, Inc., Youngstown, Ohio) for 15 minutes for monitoring the presence and localization of the transplanted cells in relation to newly formed blood vessels. In the monitoring, a fluorescence microscope BIOREVO, BZ-9000 (KEYENCE, Osaka, Japan) was used.

Isolation and Evaluation of CD31⁻ SP Cells Derived from Pig Dental Pulp, Bone Marrow, and Adipose Tissue The results of flow cytometry analysis demonstrate that SP cells derived from dental pulp, bone marrow, and adipose tissue from the same individual were present in amounts of 1.6%, 0.3%, and 0.1%, respectively, relative to the total cells (FIGS. 11A(*a*), 11B(*e*), and 11C(*i*)). In addition, it was demonstrated that CD31⁻ SP cells derived from dental pulp, bone marrow, and adipose tissue were present in amounts of 0.9%, 0.3%, and 0.1%, respectively, relative to the total cells (FIGS. 11A(*b*), 11B(*f*), and 11C(*j*)). These three CD31⁻ SP cell populations showed similar cell phenotypes, i.e., they included stellate cells with multiple long processes and spindle cells. The stellate cells had a large nucleus surrounded by granules. The spindle cell was a neuron-like cell having long and thin processes and a small amount of cytoplasm. These are shown in FIGS. 11A(*c*), A(*d*), B(*g*), B(*h*), C(*k*), and C(*l*). EBM2 containing IGF1, EGF, and 10% fetal bovine serum maintained the phenotype of the CD31⁻ SP cells. This shows that at least 99.8% of cells in the 12th passage are CD31⁻ and ABCG2/BCRP1+. A single dental pulp CD31⁻ SP cell and a single adipose CD31⁻ SP cell seeded in a 35-mm plate coated with type I collagen each formed a colony in 10 days, and a single bone marrow CD31⁻ SP cell formed a colony in 14 days. The results demonstrate that these cells have colony-forming activities. The efficiencies of attachment and growth of pig dental pulp, bone marrow, and adipose CD31⁻ SP cells were estimated to be 8%, 6%, and 7%, respectively. Limiting dilution analysis at the third passage culture showed that the frequency of dental pulp CFU of pig dental pulp CD31⁻ SP cells, pig bone marrow CD31⁻ SP cells, and pig adipose CD31⁻ SP cells were 80%, 75%, and 80%, respectively.

"Traits as a stem cell (Stemness)" of a pig dental pulp CD31⁻ SP cell were compared with those of pig bone marrow and adipose CD31⁻ SP cells by flow cytometry analysis of cell surface antibody markers. These three CD31⁻ SP cell populations of the third passage were positive for CD29, CD44, CD90, and CD105, but were negative for CD31 and CD146. The expression level of CD34 in pig dental pulp CD31⁻ SP cells was considerably higher than those in pig bone marrow CD31⁻ SP cells and pig adipose CD31⁻ SP cells. The expression levels of CXCR4 in pig dental pulp and adipose CD31⁻ SP cells were higher than that in pig bone marrow CD31⁻ SP cells. The results are shown in Table 7.

TABLE 7

|  | Pulp CD31⁻SP 4th | Bone marrow CD31⁻SP 4th | Adipose CD31⁻SP 4th |
| --- | --- | --- | --- |
| CD14 | 0% | 0.10% | 0.20% |
| CD29 | 99.2% | 99.2% | 99.4% |
| CD31 | 0.1% | 0.2% | 0% |
| CD34 | 50.0% | 21.1% | 14.3% |
| CD44 | 99.2% | 99.7% | 99.5% |
| CD73 | 88.7% | 86.6% | 83.1% |
| CD90 | 85.7% | 72.8% | 85.6% |
| CD105 | 86.3% | 86.6% | 89.8% |
| CD117 | 9.3% | 7.6% | 7.2% |
| CD133 | 0.2% | 1.9% | 1.5% |
| CD146 | 0.5% | 0.3% | 0.3% |
| CD150 | 2.8% | 5.3% | 6.7% |
| CD271 | 1.4% | 1.7% | 2.1% |
| CXCR4 | 7.8% | 4.5% | 10.1% |

Expression levels of stem cell markers, Sox2, Tert, Bmi1, CXCR4, and Stat3 mRNAs, in dental pulp CD31⁻ SP cells were comparable to those in bone marrow and adipose CD31⁻ SP cells. The results suggest that these three cell populations have the properties as stem cells comparable to each other. The angiogenic and/or neurotrophic factors, GM-CSF, MMP-3, VEGF-A, BDNF, GDNF, NGF, and neuropeptide Y were similarly expressed in all the three cell populations. The results are shown in Table 8.

TABLE 8

|  | BM/Pulp | adipose/Pulp |
| --- | --- | --- |
| Sox 2 | 2.5 | 0 |
| Tert | 1.0 | 0.2 |
| Bmi 1 | 0.8 | 1.7 |
| CXCR4 | 0.7 | 0.7 |
| Stat 3 | 1.1 | 1.9 |
| GM-CSF | 0.5 | 0.2 |
| MMP 3 | 0.8 | 1.2 |
| VEGF | 0.9 | 0.9 |
| BDNF | 2.3 | 2.5 |
| GDNF | 0.9 | 0.3 |
| NGF | 0.5 | 2.2 |

The differentiation potentials of CD31⁻ SP cells into vascular endothelial cells (FIGS. 12(*a*), (*b*), and (*c*)), and neurospheres (FIGS. 12(*d*), (*e*), and (*f*)) were compared among the three cell populations, canine dental pulp, bone marrow, and adipose CD31⁻ SP cells. Extensive networks of cords and tube-like structures were observed in all cell populations on matrigel within 12 hours of the culture (FIGS. 12(*a*), (*b*), and (*c*)). Clusters and proliferative neurospheres were detected on the 14th day after starting of culturing. The three cell populations did not show a large difference in incidence and amount of neurospheres. In addition, nerves were successfully further induced from these neurospheres. These results demonstrate that all of the three cell populations have the same blood vessel-inducing (angiogenic) and nerve-inducing (neurogenic) potentials.

Figure 13A:
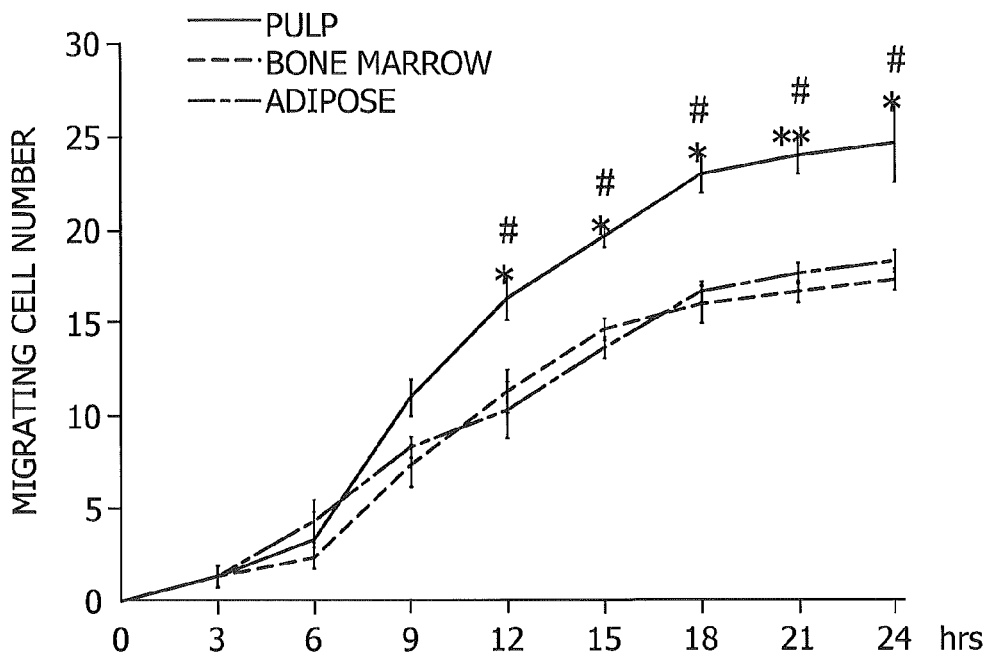
FIG. 13 shows effects of dental pulp, bone marrow, and adipose CD31$^-$ SP cells on stromal cell-derived factor 1 (SDF1). The data are each shown as mean±standard deviation of four samples. The experiment was repeated three times, and typical experimental results are shown. Statistical analysis was performed by a non-paired Student's t test. (a): migration activity on 0, 3, 6, 9, 12, 15, 18, 21, and 24 hours, supplemented with SDF-1 (10 ng/mL), *: P<0.001, dental pulp vs. bone marrow, #: P<0.05, dental pulp vs. adipose, **: P<0.001, bone marrow vs. adipose; and (b): growth activity on 2, 18, 26, and 44 hours, supplemented with SDF-1 (10 ng/mL).
Figure 13B:
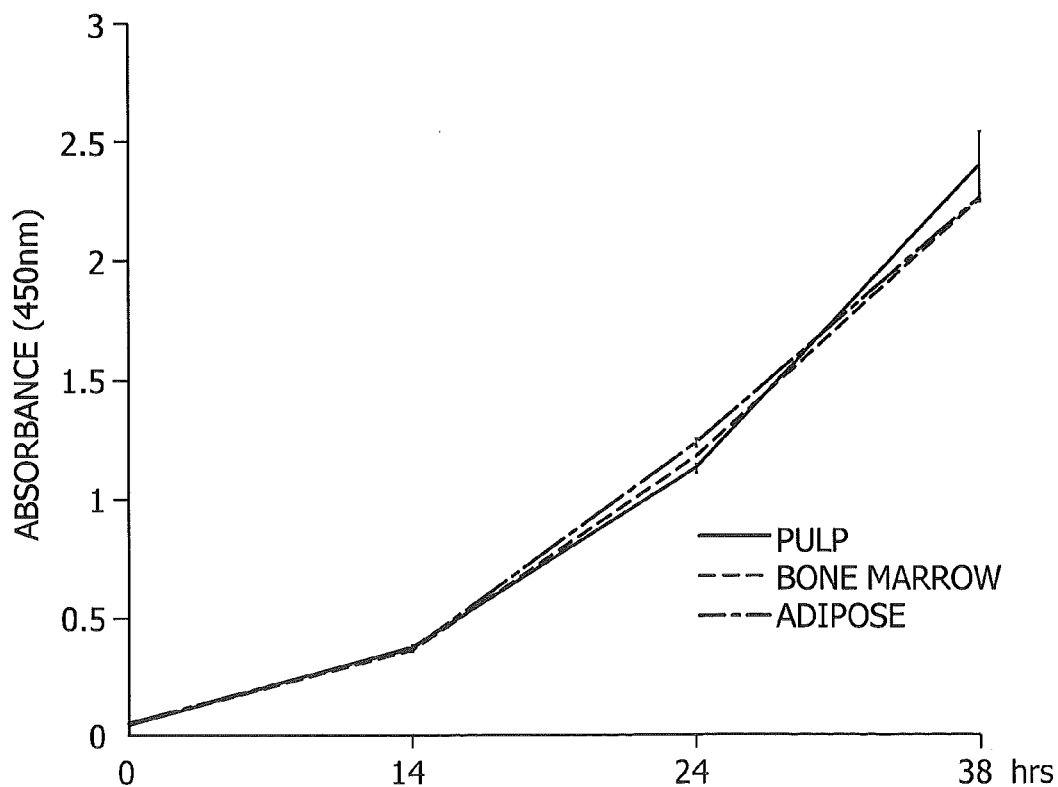

The growth activity with SDF-1 was the same in all pig dental pulp CD31⁻ SP cells and pig bone marrow and adipose CD31⁻ SP cells (FIG. 13(a)). The migration activity, which is indicated by TAXI Scan-FL, with SDF-1 was also the same in all dental pulp CD31⁻ SP cells and bone marrow and adipose CD31⁻ SP cells (FIG. 13(b)).

Figure 14A:
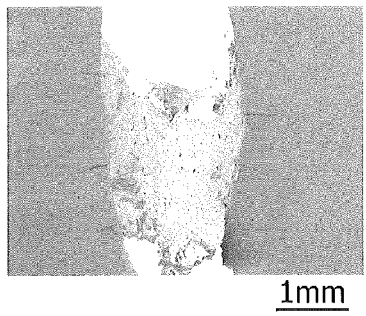
FIG. 14 shows regeneration of dental pulp after in vivo subcutaneous transplantation into immunodeficient mice (SCID mice) and includes optical microscopic images (a), (b), and (c) after transplantation of pig dental pulp CD31⁻ SP cells; (d), (e), and (f) after transplantation of pig bone marrow CD31⁻ SP cells; and (g), (h), and (i) after transplantation of pig adipose CD31⁻ SP cells, all on the 14th day after transplantation.
Figure 14B:
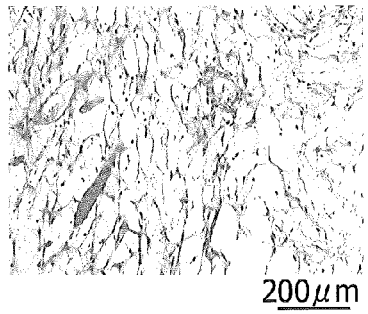
Figure 14C:
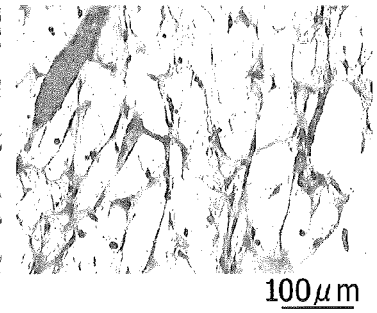
Figure 14D:
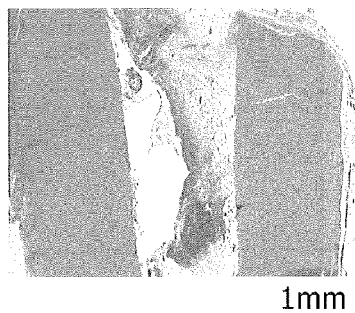
Figure 14E:
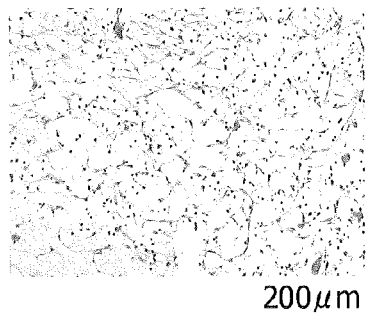
Figure 14F:
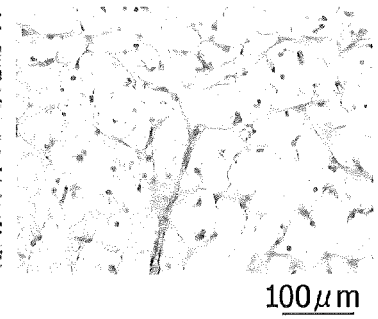
Figure 14G:
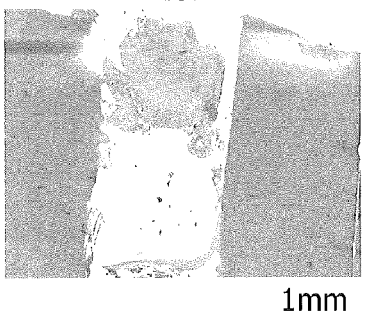
Figure 14H:
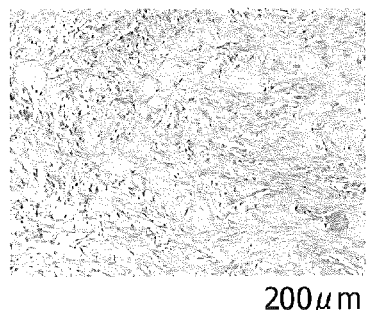
Figure 14I:
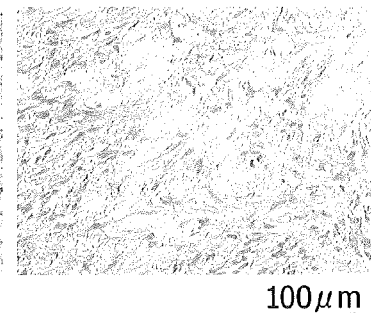

Regeneration of Dental Pulp after Subcutaneous Transplantation of Root Filled with CD31⁻ SP Cells Subsequently, in vivo subcutaneous transplantation of a root filled with CD31⁻ SP cells into a severe combined immunodeficiency (SCID) mouse was evaluated. The root canal on the 14th day after transplantation of pig dental pulp CD31⁻ SP cells was filled with dental pulp-like tissue having a sufficiently organized blood vessel system (FIGS. 14(a), (b), and (c)). Transplantation of pig bone marrow CD31⁻ SP cells also induced dental pulp-like tissue having capillary vessels (FIGS. 14(d), (e), and (f)). In transplantation of pig adipose CD31⁻ SP cells, calcification was observed (FIGS. 14(g), (h), and (i)).

EXAMPLE 3

Immunogenicity of Dental Pulp, Bone Marrow, and Adipose CD31⁻ SP Cells

Canine blood was transferred to a Venoject vacuum blood-collecting vessel (TERUMO) immediately after blood withdrawal, and the same amount of physiological saline (Otsuka Pharmaceutical Co., Ltd.) was added thereto. After end-over-end mixing, peripheral blood mononuclear cells (PBMCs) were isolated by a specific gravity centrifugal method (specific gravity: 1.007) using Lymphoprep Tube (Axis-Shield). A half of the PBMCs were treated with 10 mg/mL of mitomycin C (Nacarai Tesque) at 37° C. for 3 hours to suppress the growth while the antigenicity thereof being maintained and were used as a stimulator.

In order to compare immune modulating potentials of canine dental pulp, bone marrow, and adipose CD31⁻ SP cells, these cells were each cultured in DMEM containing 10% FBS for 3 days. The culture supernatants were then each collected and concentrated ten times with Centrifugal Filter Units (MILLI PORE) to be used. The PBMCs and the stimulator PBMCs each adjusted to $1 \times 10^5$ cells were co-cultured in RPMI1640 containing 10% FBS on a 96-well plate for 48 hours. Furthermore, the culture supernatant (conditioned medium) of dental pulp, bone marrow, or adipose CD31⁻ SP cells was added thereto. The growth activities were measured over time using Tetra Color ONE (Seikagaku Biobusiness Corporation) (MTT method), and the effects of inhibiting PBMC growth by addition of culture supernatants were compared.

Messenger RNAs involving in immunogenicities of pig dental pulp, bone marrow, and adipose CD31⁻ SP cells were investigated by real-time RT-PCR. The results thereof demonstrate that no expression of MHC (major histocompatibility complex) classes IIDRB, CD80, CD40 was observed in all of the three types of cells. In addition, the expression levels of MHC class IA in dental pulp, bone marrow, and adipose were very low, 0.07, 0.25, and 0.08, respectively, compared with those in pig unisolated total dental pulp cells. The results of flow cytometry demonstrated that CD40, CD80, CD86, and MHC class II were negative in the three types of cells, whereas MHC class I was 36.0% in dental pulp, 73.8% in bone marrow, and 80.0% in adipose. Accordingly, it was suggested that the immunogenicities of the three types of cells are low.

Immune Modulating Potential of Dental Pulp, Bone Marrow, and Adipose CD31⁻ SP cells The immune modulating potentials of canine dental pulp, bone marrow, and adipose CD31⁻ SP cells were investigated by a mixed lymphocyte reaction (MLR) method through inhibition, by the three culture supernatants, of the increase of autologous canine peripheral blood mononuclear cells caused by addition of heterologous peripheral blood mononuclear cells (no growth potential by itself). The results demonstrated that all of the dental pulp, bone marrow, and adipose CD31⁻ SP cells significantly suppress the increase of autologous peripheral blood mononuclear cells without any significant difference among three types of cells (FIG. 15). Accordingly, it was suggested that three types of cells have similar immune modulating potentials.

REFERENCE SIGNS LIST 100 target tooth
110 apical periodontitis
120 root (apical) portion
200 root canal filling material
210 extracellular matrix
220 mesenchymal stem cell
230 chemotactic factor
400 blood vessel
500 dentin
610 gelatin
620 resin
630 morphogenetic factor
640 cement
700 root (apical) portion filled with root canal filling material

The invention claimed is:

1. A root canal filling material comprising:
   an adipose stem cell including CD105-positive cells or CXCR4-positive cells; and
   an extracellular matrix.

2. The root canal filling material according to claim 1, further comprising a chemotactic factor comprising at least one of cell migration factors, cell growth factors, and neurotrophic factors.

3. The root canal filling material according to claim 2, wherein the cell migration factor is at least one of SDF-1, VEGF, GCSF, SCF, MMP3, Slit, GM-CSF, and serum.

4. The root canal filling material according to claim 2, wherein the cell growth factor is at least one of IGF, bFGF, PDGF, and serum.

5. The root canal filling material according to claim 2, wherein the neurotrophic factor is at least one of GDNF, BDNF, NGF, neuropeptide Y, neurotrophin 3, and serum.

6. The root canal filling material according to claim 1, wherein the extracellular matrix is composed of a biocompatible material comprising at least one of collagen, artificial proteoglycan, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium, and gold.

7. The root canal filling material according to claim 1, wherein the content of the adipose stem cell in the extracellular matrix is equal to or greater than $1 \times 10^3$ cells/µL and equal to or less than $1 \times 10^6$ cells/µL.

8. A method for regenerating dental tissue, comprising steps of:
   injecting the root canal filling material according to claim 1 into the apex side of a root canal subjected to pulp extirpation or to root canal enlargement; and
   cleaning an infected root canal.

9. The method for regenerating dental tissue according to claim 8, further comprising enlarging the root canal to increase the diameter of the root canal of the apex portion to a predetermined size, before the step of injecting the root canal filling material into the apical side of the root canal.

* * * * *

SEQUENCE LISTING

<160> NUMBER OF SEQ ID NOS: 62

<210> SEQ ID NO 1
<211> LENGTH: 20
<212> TYPE: DNA
<213> ORGANISM: Artificial Sequence
<220> FEATURE:
<223> OTHER INFORMATION: Canine forward primer for Sox2

<400> SEQUENCE: 1
agctagtctc caagcgacga                                          20

```
<210> SEQ ID NO 2
<211> LENGTH: 20
<212> TYPE: DNA
<213> ORGANISM: Artificial Sequence
<220> FEATURE:
<223> OTHER INFORMATION: Canine reverse primer for Sox2

<400> SEQUENCE: 2
ccacgtttgc aactgtccta                                                  20

<210> SEQ ID NO 3
<211> LENGTH: 20
<212> TYPE: DNA
<213> ORGANISM: Artificial Sequence
<220> FEATURE:
<223> OTHER INFORMATION: Canine forward primer Bmi1

<400> SEQUENCE: 3
cactcccgtt cagtctcctc                                                  20

<210> SEQ ID NO 4
<211> LENGTH: 20
<212> TYPE: DNA
<213> ORGANISM: Artificial Sequence
<220> FEATURE:
<223> OTHER INFORMATION: Canine reverse primer for Bmi1

<400> SEQUENCE: 4
ccagatgaag ttgctgacga                                                  20

<210> SEQ ID NO 5
<211> LENGTH: 20
<212> TYPE: DNA
<213> ORGANISM: Artificial Sequence
<220> FEATURE:
<223> OTHER INFORMATION: Canine forward primer for CXCR4

<400> SEQUENCE: 5
ctgtggcaaa ctggtacttc                                                  20

<210> SEQ ID NO 6
<211> LENGTH: 20
<212> TYPE: DNA
<213> ORGANISM: Artificial Sequence
<220> FEATURE:
<223> OTHER INFORMATION: Canine reverse primer for CXCR4

<400> SEQUENCE: 6
tcaacaggag ggcaggtatc                                                  20

<210> SEQ ID NO 7
<211> LENGTH: 20
<212> TYPE: DNA
<213> ORGANISM: Artificial Sequence
<220> FEATURE:
<223> OTHER INFORMATION: Canine forward primer for Stat3

<400> SEQUENCE: 7
gtggtgacgg agaagcaaca                                                  20

<210> SEQ ID NO 8
<211> LENGTH: 20
<212> TYPE: DNA
<213> ORGANISM: Artificial Sequence
<220> FEATURE:
<223> OTHER INFORMATION: Canine reverse primer for Stat3
```

```
<400> SEQUENCE: 8
ttctgtctgg tcaccgactg                                        20

<210> SEQ ID NO 9
<211> LENGTH: 20
<212> TYPE: DNA
<213> ORGANISM: Artificial Sequence
<220> FEATURE:
<223> OTHER INFORMATION: Canine forward primer for GM-CSF

<400> SEQUENCE: 9
gcagaacctg cttttcttgg                                        20

<210> SEQ ID NO 10
<211> LENGTH: 20
<212> TYPE: DNA
<213> ORGANISM: Artificial Sequence
<220> FEATURE:
<223> OTHER INFORMATION: Canine reverse primer for GM-CSF

<400> SEQUENCE: 10
ccctcagggt caaacacttc                                        20

<210> SEQ ID NO 11
<211> LENGTH: 20
<212> TYPE: DNA
<213> ORGANISM: Artificial Sequence
<220> FEATURE:
<223> OTHER INFORMATION: Canine forward primer for MMP3

<400> SEQUENCE: 11
ccctctgatt cctccaatga                                        20

<210> SEQ ID NO 12
<211> LENGTH: 20
<212> TYPE: DNA
<213> ORGANISM: Artificial Sequence
<220> FEATURE:
<223> OTHER INFORMATION: Canine reverse primer for MMP3

<400> SEQUENCE: 12
ggatggccaa aatgaagaga                                        20

<210> SEQ ID NO 13
<211> LENGTH: 20
<212> TYPE: DNA
<213> ORGANISM: Artificial Sequence
<220> FEATURE:
<223> OTHER INFORMATION: Canine forward primer for VEGF-A

<400> SEQUENCE: 13
ctacctccac catgccaagt                                        20

<210> SEQ ID NO 14
<211> LENGTH: 20
<212> TYPE: DNA
<213> ORGANISM: Artificial Sequence
<220> FEATURE:
<223> OTHER INFORMATION: Canine reverse primer for VEGF-A

<400> SEQUENCE: 14
acgcaggatg gcttgaagat                                        20

<210> SEQ ID NO 15
<211> LENGTH: 20
```

```
<212> TYPE: DNA
<213> ORGANISM: Artificial Sequence
<220> FEATURE:
<223> OTHER INFORMATION: Canine forward primer for BDNF

<400> SEQUENCE: 15
gttggccgac acttttgaac                                            20

<210> SEQ ID NO 16
<211> LENGTH: 20
<212> TYPE: DNA
<213> ORGANISM: Artificial Sequence
<220> FEATURE:
<223> OTHER INFORMATION: Canine reverse primer for BDNF

<400> SEQUENCE: 16
cctcatcgac atgtttgcag                                            20

<210> SEQ ID NO 17
<211> LENGTH: 19
<212> TYPE: DNA
<213> ORGANISM: Artificial Sequence
<220> FEATURE:
<223> OTHER INFORMATION: Canine forward primer for GDNF

<400> SEQUENCE: 17
gccgagcagt gactcaaac                                             19

<210> SEQ ID NO 18
<211> LENGTH: 19
<212> TYPE: DNA
<213> ORGANISM: Artificial Sequence
<220> FEATURE:
<223> OTHER INFORMATION: Canine reverse primer for GDNF

<400> SEQUENCE: 18
tctcgggtga ccttttcag                                             19

<210> SEQ ID NO 19
<211> LENGTH: 20
<212> TYPE: DNA
<213> ORGANISM: Artificial Sequence
<220> FEATURE:
<223> OTHER INFORMATION: Canine forward primer for NGF

<400> SEQUENCE: 19
caacaggact cacaggagca                                            20

<210> SEQ ID NO 20
<211> LENGTH: 20
<212> TYPE: DNA
<213> ORGANISM: Artificial Sequence
<220> FEATURE:
<223> OTHER INFORMATION: Canine reverse primer for NGF

<400> SEQUENCE: 20
atgttcacct ctcccagcac                                            20

<210> SEQ ID NO 21
<211> LENGTH: 20
<212> TYPE: DNA
<213> ORGANISM: Artificial Sequence
<220> FEATURE:
<223> OTHER INFORMATION: Canine forward primer for beta-actin

<400> SEQUENCE: 21
```
aagtacccca ttgagcacgg                                              20

<210> SEQ ID NO 22
<211> LENGTH: 20
<212> TYPE: DNA
<213> ORGANISM: Artificial Sequence
<220> FEATURE:
<223> OTHER INFORMATION: Canine reverse primer for beta-actin

<400> SEQUENCE: 22
atcacgatgc cagtggtgcg                                              20

<210> SEQ ID NO 23
<211> LENGTH: 20
<212> TYPE: DNA
<213> ORGANISM: Artificial Sequence
<220> FEATURE:
<223> OTHER INFORMATION: Canine forward primer for Syndecan 3

<400> SEQUENCE: 23
tcatgcagga cagcttcaac                                              20

<210> SEQ ID NO 24
<211> LENGTH: 20
<212> TYPE: DNA
<213> ORGANISM: Artificial Sequence
<220> FEATURE:
<223> OTHER INFORMATION: Canine reverse primer for Syndecan 3

<400> SEQUENCE: 24
agggctggaa tctagggaaa                                              20

<210> SEQ ID NO 25
<211> LENGTH: 20
<212> TYPE: DNA
<213> ORGANISM: Artificial Sequence
<220> FEATURE:
<223> OTHER INFORMATION: Canine forward primer for Tenascin-C

<400> SEQUENCE: 25
tggctgtctt ggacacagag                                              20

<210> SEQ ID NO 26
<211> LENGTH: 20
<212> TYPE: DNA
<213> ORGANISM: Artificial Sequence
<220> FEATURE:
<223> OTHER INFORMATION: Canine reverse primer for Tenascin-C

<400> SEQUENCE: 26
gactccagag ttggggtctg                                              20

<210> SEQ ID NO 27
<211> LENGTH: 20
<212> TYPE: DNA
<213> ORGANISM: Artificial Sequence
<220> FEATURE:
<223> OTHER INFORMATION: Canine forward primer for Vimentin

<400> SEQUENCE: 27
ggagcagcag aacaagatcc                                              20

<210> SEQ ID NO 28
<211> LENGTH: 20
<212> TYPE: DNA
<213> ORGANISM: Artificial Sequence

```
<220> FEATURE:
<223> OTHER INFORMATION: Canine reverse primer for Vimentin

<400> SEQUENCE: 28
tctcggcttc ctctctctga                                            20

<210> SEQ ID NO 29
<211> LENGTH: 19
<212> TYPE: DNA
<213> ORGANISM: Artificial Sequence
<220> FEATURE:
<223> OTHER INFORMATION: Canine forward primer for ALPase

<400> SEQUENCE: 29
ccatcctgta tggcaatgg                                             19

<210> SEQ ID NO 30
<211> LENGTH: 22
<212> TYPE: DNA
<213> ORGANISM: Artificial Sequence
<220> FEATURE:
<223> OTHER INFORMATION: Canine reverse primer for ALPase

<400> SEQUENCE: 30
tgaacgagag aatgtctcca tg                                         22

<210> SEQ ID NO 31
<211> LENGTH: 20
<212> TYPE: DNA
<213> ORGANISM: Artificial Sequence
<220> FEATURE:
<223> OTHER INFORMATION: Canine forward primer for Periostin

<400> SEQUENCE: 31
aaaccattgg aggcaaacag                                            20

<210> SEQ ID NO 32
<211> LENGTH: 20
<212> TYPE: DNA
<213> ORGANISM: Artificial Sequence
<220> FEATURE:
<223> OTHER INFORMATION: Canine reverse primer for Periostin

<400> SEQUENCE: 32
tgcagcttca agtaggctga                                            20

<210> SEQ ID NO 33
<211> LENGTH: 20
<212> TYPE: DNA
<213> ORGANISM: Artificial Sequence
<220> FEATURE:
<223> OTHER INFORMATION: Canine forward primer for PLAP-1

<400> SEQUENCE: 33
tcccgtcagg attacaggag                                            20

<210> SEQ ID NO 34
<211> LENGTH: 20
<212> TYPE: DNA
<213> ORGANISM: Artificial Sequence
<220> FEATURE:
<223> OTHER INFORMATION: Canine reverse primer for PLAP-1

<400> SEQUENCE: 34
gaacgctcat tctgctcaca                                            20
```

```
<210> SEQ ID NO 35
<211> LENGTH: 20
<212> TYPE: DNA
<213> ORGANISM: Artificial Sequence
<220> FEATURE:
<223> OTHER INFORMATION: Canine forward primer for ap2

<400> SEQUENCE: 35
cggatgacag aaaagtcaag                                                 20

<210> SEQ ID NO 36
<211> LENGTH: 20
<212> TYPE: DNA
<213> ORGANISM: Artificial Sequence
<220> FEATURE:
<223> OTHER INFORMATION: Canine reverse primer for ap2

<400> SEQUENCE: 36
ttcagcttga tgtcccttgg                                                 20

<210> SEQ ID NO 37
<211> LENGTH: 20
<212> TYPE: DNA
<213> ORGANISM: Artificial Sequence
<220> FEATURE:
<223> OTHER INFORMATION: Canine forward primer for DSPP

<400> SEQUENCE: 37
gtcctagtgg gaatggagca                                                 20

<210> SEQ ID NO 38
<211> LENGTH: 20
<212> TYPE: DNA
<213> ORGANISM: Artificial Sequence
<220> FEATURE:
<223> OTHER INFORMATION: Canine reverse primer for DSPP

<400> SEQUENCE: 38
tcttcagggc catcatcttc                                                 20

<210> SEQ ID NO 39
<211> LENGTH: 20
<212> TYPE: DNA
<213> ORGANISM: Artificial Sequence
<220> FEATURE:
<223> OTHER INFORMATION: Porcine forward primer for Sox2

<400> SEQUENCE: 39
aatgccttca tggtgtggtc                                                 20

<210> SEQ ID NO 40
<211> LENGTH: 20
<212> TYPE: DNA
<213> ORGANISM: Artificial Sequence
<220> FEATURE:
<223> OTHER INFORMATION: Porcine reverse primer for Sox2

<400> SEQUENCE: 40
cggggccggt atttataatc                                                 20

<210> SEQ ID NO 41
<211> LENGTH: 18
<212> TYPE: DNA
<213> ORGANISM: Artificial Sequence
<220> FEATURE:
<223> OTHER INFORMATION: Porcine forward primer for Tert
```

<400> SEQUENCE: 41
caggtgtacc gcctcctg                                                    18

<210> SEQ ID NO 42
<211> LENGTH: 20
<212> TYPE: DNA
<213> ORGANISM: Artificial Sequence
<220> FEATURE:
<223> OTHER INFORMATION: Porcine reverse primer for Tert

<400> SEQUENCE: 42
ccagatgcag tcttgcactt                                                  20

<210> SEQ ID NO 43
<211> LENGTH: 20
<212> TYPE: DNA
<213> ORGANISM: Artificial Sequence
<220> FEATURE:
<223> OTHER INFORMATION: Porcine forward primer for Bmi1

<400> SEQUENCE: 43
atatttacgg tgcccagcag                                                  20

<210> SEQ ID NO 44
<211> LENGTH: 20
<212> TYPE: DNA
<213> ORGANISM: Artificial Sequence
<220> FEATURE:
<223> OTHER INFORMATION: Porcine reverse primer for Bmi1

<400> SEQUENCE: 44
gaagtggccc attccttctc                                                  20

<210> SEQ ID NO 45
<211> LENGTH: 20
<212> TYPE: DNA
<213> ORGANISM: Artificial Sequence
<220> FEATURE:
<223> OTHER INFORMATION: Porcine forward primer for CXCR4

<400> SEQUENCE: 45
ccgtggcaaa ctggtacttt                                                  20

<210> SEQ ID NO 46
<211> LENGTH: 20
<212> TYPE: DNA
<213> ORGANISM: Artificial Sequence
<220> FEATURE:
<223> OTHER INFORMATION: Porcine reverse primer for CXCR4

<400> SEQUENCE: 46
tcaacaggag ggcaggtatc                                                  20

<210> SEQ ID NO 47
<211> LENGTH: 20
<212> TYPE: DNA
<213> ORGANISM: Artificial Sequence
<220> FEATURE:
<223> OTHER INFORMATION: Porcine forward primer for Stat3

<400> SEQUENCE: 47
gtggtgacag agaagcagca                                                  20

<210> SEQ ID NO 48

```
<211> LENGTH: 20
<212> TYPE: DNA
<213> ORGANISM: Artificial Sequence
<220> FEATURE:
<223> OTHER INFORMATION: Porcine reverse primer for Stat3

<400> SEQUENCE: 48
ttctgcctgg tcactgactg                                          20

<210> SEQ ID NO 49
<211> LENGTH: 20
<212> TYPE: DNA
<213> ORGANISM: Artificial Sequence
<220> FEATURE:
<223> OTHER INFORMATION: Porcine forward primer for GM-CSF

<400> SEQUENCE: 49
tgtggatgcc atcaaagaag                                          20

<210> SEQ ID NO 50
<211> LENGTH: 20
<212> TYPE: DNA
<213> ORGANISM: Artificial Sequence
<220> FEATURE:
<223> OTHER INFORMATION: Porcine reverse primer for GM-CSF

<400> SEQUENCE: 50
gtgctgctca tagtgcttgg                                          20

<210> SEQ ID NO 51
<211> LENGTH: 20
<212> TYPE: DNA
<213> ORGANISM: Artificial Sequence
<220> FEATURE:
<223> OTHER INFORMATION: Porcine forward primer for MMP3

<400> SEQUENCE: 51
acccagatgt ggagttcctg                                          20

<210> SEQ ID NO 52
<211> LENGTH: 21
<212> TYPE: DNA
<213> ORGANISM: Artificial Sequence
<220> FEATURE:
<223> OTHER INFORMATION: Porcine reverse primer for MMP3

<400> SEQUENCE: 52
ggagtcactt cctcccagat t                                        21

<210> SEQ ID NO 53
<211> LENGTH: 20
<212> TYPE: DNA
<213> ORGANISM: Artificial Sequence
<220> FEATURE:
<223> OTHER INFORMATION: Porcine forward primer for VEGF-A

<400> SEQUENCE: 53
ctacctccac catgccaagt                                          20

<210> SEQ ID NO 54
<211> LENGTH: 20
<212> TYPE: DNA
<213> ORGANISM: Artificial Sequence
<220> FEATURE:
<223> OTHER INFORMATION: Porcine reverse primer for VEGF-A

<400> SEQUENCE: 54
```
acacaggacg gcttgaagat                    20

<210> SEQ ID NO 55
<211> LENGTH: 23
<212> TYPE: DNA
<213> ORGANISM: Artificial Sequence
<220> FEATURE:
<223> OTHER INFORMATION: Porcine forward primer for BDNF

<400> SEQUENCE: 55
ttcaagaggc ctgacatcgt cgt                23

<210> SEQ ID NO 56
<211> LENGTH: 20
<212> TYPE: DNA
<213> ORGANISM: Artificial Sequence
<220> FEATURE:
<223> OTHER INFORMATION: Porcine reverse primer for BDNF

<400> SEQUENCE: 56
agaagaggag gctccaaagg                    20

<210> SEQ ID NO 57
<211> LENGTH: 20
<212> TYPE: DNA
<213> ORGANISM: Artificial Sequence
<220> FEATURE:
<223> OTHER INFORMATION: Porcine forward primer for GDNF

<400> SEQUENCE: 57
acggccatac acctcaatgt                    20

<210> SEQ ID NO 58
<211> LENGTH: 20
<212> TYPE: DNA
<213> ORGANISM: Artificial Sequence
<220> FEATURE:
<223> OTHER INFORMATION: Porcine reverse primer for GDNF

<400> SEQUENCE: 58
ccgtctgttt ttggacaggt                    20

<210> SEQ ID NO 59
<211> LENGTH: 20
<212> TYPE: DNA
<213> ORGANISM: Artificial Sequence
<220> FEATURE:
<223> OTHER INFORMATION: Porcine forward primer for NGF

<400> SEQUENCE: 59
tggtgttggg agaggtgaat                    20

<210> SEQ ID NO 60
<211> LENGTH: 19
<212> TYPE: DNA
<213> ORGANISM: Artificial Sequence
<220> FEATURE:
<223> OTHER INFORMATION: Porcine reverse primer for NGF

<400> SEQUENCE: 60
ccgtgtcgat tcggataaa                     19

<210> SEQ ID NO 61
<211> LENGTH: 20
<212> TYPE: DNA

```
<213> ORGANISM: Artificial Sequence
<220> FEATURE:
<223> OTHER INFORMATION: Porcine forward primer for beta-actin

<400> SEQUENCE: 61
ctcttccagc cctccttcct                                              20

<210> SEQ ID NO 62
<211> LENGTH: 20
<212> TYPE: DNA
<213> ORGANISM: Artificial Sequence
<220> FEATURE:
<223> OTHER INFORMATION: Porcine reverse primer for beta-actin

<400> SEQUENCE: 62
acgtcgcact tcatgatcga                                              20
```